United States Patent
Chu et al.

(10) Patent No.: US 12,264,655 B2
(45) Date of Patent: Apr. 1, 2025

(54) UNIPOLAR ARTIFICIAL MUSCLES AND METHODS OF USE THEREOF

(71) Applicant: BOARD OF REGENTS, THE UNIVERSITY OF TEXAS SYSTEM, Austin, TX (US)

(72) Inventors: Hetao Chu, Chengdu (CN); Jinsong Leng, Harbin (CN); Ray H. Baughman, Dallas, TX (US); Xinghao Hu, Plano, TX (US); Na Li, Milwaukee, WI (US); Carter S. Haines, Murphy, TX (US); Shaoli Fang, Richardson, TX (US); Zhong Wang, Dallas, TX (US); Jiuke Mu, Plano, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 800 days.

(21) Appl. No.: 17/380,746

(22) PCT Filed: Feb. 3, 2020

(86) PCT No.: PCT/US2020/016391
§ 371 (c)(1),
(2) Date: Jul. 20, 2021

(87) PCT Pub. No.: WO2020/163228
PCT Pub. Date: Aug. 31, 2020

(65) Prior Publication Data
US 2023/0141697 A1    May 11, 2023

Related U.S. Application Data

(60) Provisional application No. 62/802,589, filed on Feb. 7, 2019.

(51) Int. Cl.
*D02G 3/16* (2006.01)
*D02G 3/26* (2006.01)
(Continued)

(52) U.S. Cl.
CPC ............... *F03G 7/025* (2021.08); *D02G 3/16* (2013.01); *D02G 3/26* (2013.01); *D02G 3/441* (2013.01);
(Continued)

(58) Field of Classification Search
CPC ............ H02N 2/00; D02G 3/16; D02G 3/441; D02G 3/26; F03G 7/029; F03G 7/005;
(Continued)

(56) References Cited

U.S. PATENT DOCUMENTS

| | | | |
|---|---|---|---|
| 2008/0170982 A1* | 7/2008 | Zhang | C01B 32/154 423/447.3 |
| 2015/0152852 A1* | 6/2015 | Li | D04C 1/02 60/527 |

(Continued)

FOREIGN PATENT DOCUMENTS

| | | |
|---|---|---|
| EP | 2833542 A1 | 2/2015 |
| WO | 2010019942 A2 | 2/2010 |

OTHER PUBLICATIONS

Officer Johannes Buter; PCT/2020/016391; International Search Report and Written Opinion; mailing date May 13, 2020; 18 pages.
(Continued)

*Primary Examiner* — Alexander A Singh
(74) *Attorney, Agent, or Firm* — Dickinson Wright PLLC; Ross Spencer Garsson

(57) ABSTRACT

Previous electrochemically-powered yarn muscles cannot be usefully operated between extreme negative and extreme positive potentials, since strokes during electron injection and during hole injection partially cancel because they are in
(Continued)

the same direction. Unipolar-stroke carbon nanotube yarn muscles are described in which muscle strokes are additive between extreme negative and extreme positive potentials, and stroke increases with potential scan rate. These electrochemical artificial muscles include an electrically conducting twisted or coiled yarn and a material that dramatically shifts the potential of zero charge of the electrochemically actuated yarn.

19 Claims, 18 Drawing Sheets

(51) Int. Cl.
*D02G 3/44* (2006.01)
*F03G 7/00* (2006.01)

(52) U.S. Cl.
CPC .............. *F03G 7/012* (2021.08); *F03G 7/029* (2021.08); *D10B 2101/122* (2013.01); *D10B 2401/16* (2013.01)

(58) Field of Classification Search
CPC ......... F03G 7/025; F03G 7/012; H01B 1/127; H01B 1/04; A61F 2002/5066; D10B 2401/16; D10B 2101/122
See application file for complete search history.

(56) References Cited

U.S. PATENT DOCUMENTS

2018/0327937 A1\* 11/2018 Di .......................... D02G 3/04
2020/0208614 A1\* 7/2020 Baughman ............. D02G 3/441

OTHER PUBLICATIONS

Baughman, et al.; Carbon Nanotube Actuators; XP-002270608; Science, vol. 284, May 21, 1999, www.sciencemag.org; pp. 1340-1344.

Foroughi, et al.; Torsional Carbon Nanotube Artificial Muscles; Science, vol. 334, Oct. 28, 2011, www.sciencemag.org; pp. 494-497.

Samatham, et al.; Active Polymers: An Overview, Electroactive Polymers for Robotic Applications, Artificial Muscles and Sensors; pp. 1-281.

\* cited by examiner

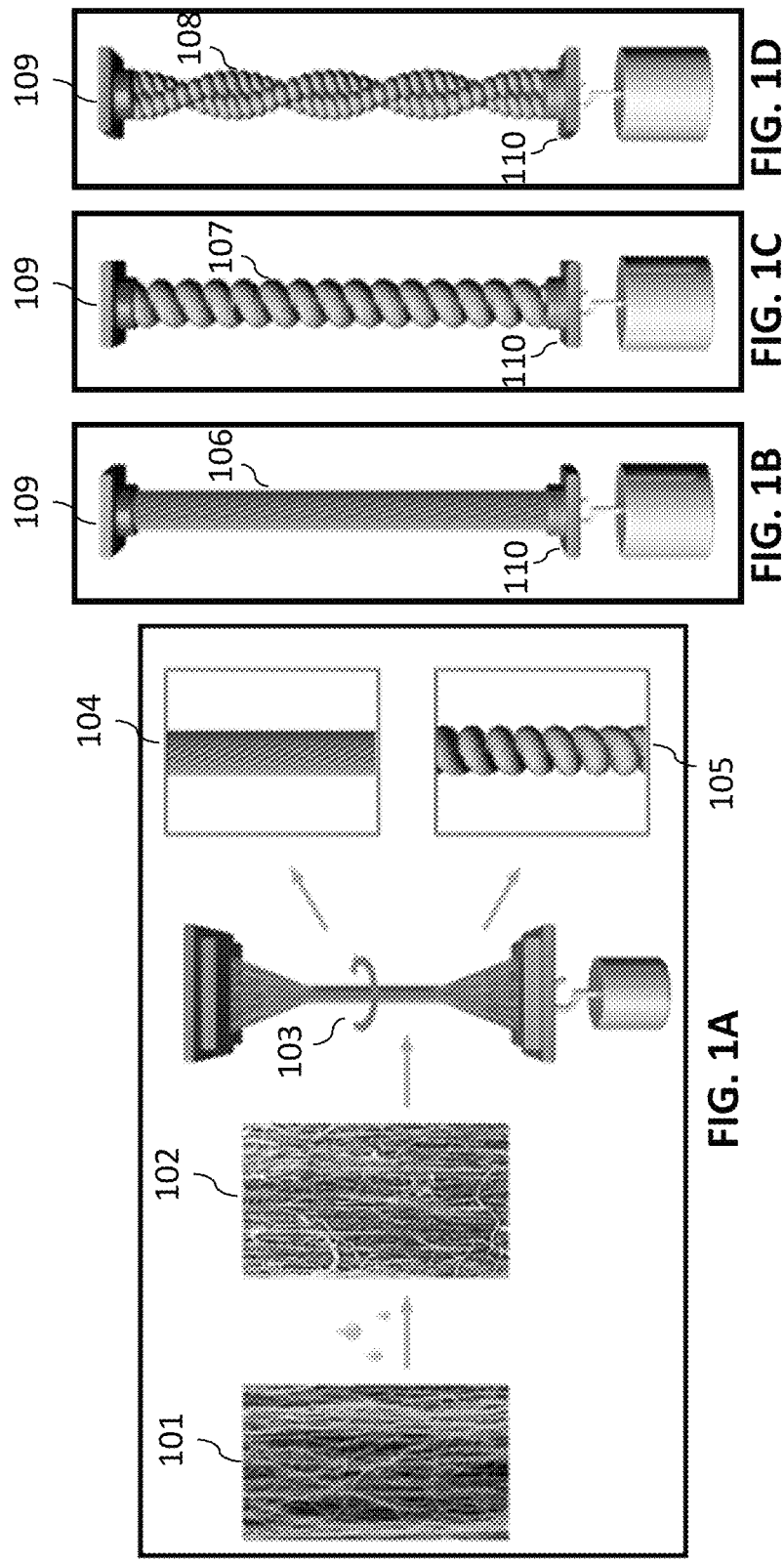

UNIPOLAR ARTIFICIAL MUSCLES AND METHODS OF USE THEREOF

CROSS-REFERENCE TO RELATED APPLICATIONS

This Application for Patent is a 35 U.S.C § 371 national application of PCT Application No. PCT/US20/16391, filed on Feb. 3, 2020, entitled "Unipolar Artificial Muscles And Methods Of Use Thereof," which claims priority to United States Provisional Patent Application No. 62/802,589, entitled "Inverted-Stroke Artificial Muscles And Methods of Use Thereof," filed Feb. 7, 2019, which provisional application (including appendices) is incorporated by reference herein in its entirety.

GOVERNMENT INTEREST

This invention was made with government support under grants FA9550-15-1-0089 and FA9550-18-1-0510 awarded by the Air Force Office of Scientific Research. The government has certain rights in the invention. This invention was also made with support under grant AT-0029 awarded by the Robert A. Welch Foundation.

FIELD OF INVENTION

The present invention is directed to unipolar-stroke artificial muscles and methods of use thereof.

BACKGROUND OF THE INVENTION

Electrothermally-powered carbon nanotube yarn muscles can generate 29 times higher specific work (1.36 J/g) and 150 times higher stress (84 MPa) than a similarly sized human muscle [Lima 2012]. Inexpensive coiled polymer artificial muscles made from fishing line and sewing thread have large tensile stroke (49%) and high specific power (5.3 kW/kg) when thermally powered [Haines 2014]. Coiled thermally-powered shape-memory alloys (SMAs) can contract by up to 8% in length, but they have large thermal hysteresis (~20° C.) and high fabrication cost ($200-300 kg$^{-1}$) [Hunter A 1992]. Although these thermally-powered artificial muscles can deliver impressive power and work during contraction, the associated long cooling time and present low energy conversion efficiency (much less than the Carnot efficiency) restrict their use for both high frequency applications and high-energy-consumption, autonomous systems. Therefore, a non-thermal, high-efficiency mechanism is needed for artificial muscles.

Electrochemically-powered artificial muscles have the advantage over electrothermally-driven or thermally driven muscles, since their efficiency is not Carnot limited. Also, it is easier to reclaim electrical energy than thermal energy during the reverse part of an actuation cycle. However, previous electrochemical carbon nanotube yarn muscles provide the same sign torsional and tensile strokes for both positive and negative potentials, resulting in partial stroke cancellation when scanned from extreme positive voltages to extreme negative voltages [Lima 2012; Foroughi 2011]. Therefore, the entire electrochemical window of the electrolyte cannot be effectively utilized.

SUMMARY OF INVENTION

The present invention provides unipolar-stroke carbon nanotube yarn muscles in which muscle stroke is additive over the entire electrochemical stability window. These muscles can alternatively be called inverted-stroke muscles. These unipolar muscles are advantageous over electrochemically-powered carbon nanotube yarn muscles, which cannot be usefully operated between extreme negative potentials and positive potentials, since strokes during electron injection and during hole injection are in the same direction. Artificial muscles that provide this undesirable stroke cancellation are referred to as "bipolar muscles," herein.

These unipolar muscles are advantageous over previous high-performance bipolar artificial muscles, which contract less when cycled fast using high potential scan rates. More specifically, some of the unipolar muscle provide scan rate enhanced stroke (SRES), which means that muscle stroke increases with increased potential scan rate, until a peak in muscle stroke occurs.

In general, in one aspect, the invention features an electrochemical artificial muscle. The electrochemical artificial muscle includes an actuating electrode that includes a first twisted yarn or coiled yarn that is electrically conducting. The electrochemical artificial muscle further includes an electronically conducting counter electrode. The electrochemical artificial muscle further includes an ionic conductor that provides a path for ionic conduction between said actuating electrode and said counter electrode. The electrochemical artificial muscle further includes a material that shifts the potential of zero charge of the actuating electrode. The shift in potential increases the potential range over which the actuating electrode monotonically increases or monotonically decreases actuator stroke during increase in potential.

Implementations of the invention can include one or more of the following features:

The first twisted yarn or coiled yarn can be (i) an electronically conducting twisted yarn or coiled yarn or (ii) a twisted yarn or coiled yarn having an electrically conducting sheath The first twisted or coiled yarn can have a capacitance of at least 0.1 F/g.

The capacitance of the first twisted or coiled yarn can be at least 1 F/g.

The first twisted or coiled yarn in the electrochemical artificial muscle can have a monotonic potential range fraction of at least 0.7.

The monotonic potential range fraction can be 1.

The first twisted or coiled yarn is a twisted and coiled yarn in which a twisted yarn is coiled.

The twisted and coiled yarn can have a spring index below 1.5.

The twisted and coiled yarn can have a spring index above 3.

The twisted and coiled yarn can have a chirality which is same to the chirality of twist of the twisted and coiled yarn.

The twisted and coiled yarn can have a chirality of coiling that is opposite to the chirality of yarn twist before coiling.

The electrochemical artificial muscle can be surrounded by electrolyte including a solvating specifies. The electrochemical artificial muscle can operate in the electrolyte.

The electrochemical artificial muscle can have an actuator stroke that increases over a potential scan rate range with increasing potential scan rate, as a result of the material and the electrolyte surrounding the electrochemical artificial muscle.

The material can include at least 10% of the total mass of the first twisted yarn or coiled yarn.

The material can be at least partially covalently attached, directly or indirectly, to the first twisted yarn or coiled yarn.

The material that is at least partially covalently attached can be selected from a group consisting of oxygen, nitrogen, boron, sulfur, and combinations thereof.

The material can be an ion-exchange material.

The ion-exchange material can be an organic polymer.

The material can include a layer of organic or inorganic material that is not substantially directly or indirectly covalently attached to the actuating electrode.

The layer can be selected from a group consisting of organic or inorganic materials containing negatively charged functionalities. The range of potentials where cations can be injected to compensate negative electronic charges on said actuating electrode can be increased due to the presence of the layer.

The layer can be selected from a group consisting of organic or inorganic materials containing positively charged functionalities. The range of potentials where anions can be injected to compensate positive electronic charges on said actuating electrode can be increased due to the presence of said layer.

The layer can be selected from a group of organic or inorganic materials containing bonded charged functionalities selected from a group consisting of a positively-charged amino group, a positively-charged nitrogen-containing group, a positively-charged sulfur-containing group, a positively-charged metal-containing group, a negatively-charged sulfonate group, a negatively-charged carboxyl group, a negatively-charged phosphate group, and combinations thereof.

The electrochemical artificial muscle can be coiled and can be operable to provide a tensile stroke of at least 2% when electrochemically charged in an aqueous electrolyte.

The electrochemical artificial muscle can be coiled and can be operable to provide a tensile stroke of at least 2% when electrochemically charged in a non-aqueous electrolyte.

The material can include an ionic polymer.

The ionic polymer can include a substituent selected from a group consisting of sulfonate and diallyldimethylammonium.

The electrochemical artificial muscle can include two or more constituent actuating electrodes. One or more constituent actuating electrodes can operate as an anode. One or more constituent actuating electrodes can operate as a cathode. The anode and cathode actuating electrodes can be connected through an ionic conductor.

The constituent actuating electrodes can be mechanically coupled together.

The electronically conducting counter electrode can include a second yarn.

The electrochemical artificial muscle can further include at least two electrolytes. The material can include one of the at least two electrolytes.

The second twisted yarn or coiled yarn can include a twisted, electrically conducting nanofiber yarn. The material can be a layer on the electrically conducting nanofibers of the nanofiber yarn.

The electrochemical artificial muscle can further include at least three electrolytes. At least one of the at least three electrolytes can be an anion-exchange material. At least one of the at least three electrolytes can be a cation-exchange material. The anion-exchange material can be incorporated into one of the actuator electrode and the electronically conducting counter electrode. The cation-exchange material can incorporated into the other of the actuator electrode and the electronically conducting counter electrode.

The electrochemical artificial muscle can be operated as a tensile muscle. Opposite muscle ends of the electrochemical artificial muscle can be tethered to prohibit relative rotation.

The electrochemical artificial muscle can be operated as a torsional muscle. Opposite muscle ends of the electrochemical artificial muscle can be not tethered to prohibit relative rotation.

The electrochemical artificial muscle can further include an electrolyte that comprises ions selected from the group consisting of alkali metal cations, halide anions, tetraalkylammonium cations, $BF_4^-$, $PF_6^-$, bis(trifluoromethanesulfonyl)imide anions, 1-butyl-1-methylpyrrolidinium cations, sulfate anions, and combinations thereof.

The actuating electrode can include substances selected from the group consisting of carbon nanotubes, graphene, graphitized nanofibers, carbon nanohorns, fullerenes, activated carbon, carbon black, and combinations thereof.

In general, in another aspect, the invention features a method that includes using one of the above-described electrochemical artificial muscles as an actuator.

BRIEF DESCRIPTION OF THE DRAWINGS

FIGS. 1A-1G show yarn fabrication and morphology. FIG. 1A shows schematic illustrations (from left to right) of the pristine CNT sheet, the CNT sheet infiltrated by polyelectrolyte, and twist insertion into this infiltrated sheet to make either twisted or twisted and coiled yarns. FIGS. 1B-1D are illustrations showing, respectively, torsional-tethered muscle configurations for polyelectrolyte infiltrated (FIG. 1B) non-coiled yarn, (FIG. 1C) coiled yarn, and (FIG. 1D) two-ply coiled yarn. FIGS. 1E-1F are scanning electron microscope (SEM) images of (FIG. 1E) an aligned neat CNT sheet before polyelectrolyte infiltrating with PSS (left) and a PSS infiltrated CNT sheet (right), where the arrows indicate the alignment direction of the CNTs in the sheets; and (FIG. 1F) a two-ply coiled CNT yarn (left) and a coiled PSS@CNT yarn (right). (Carbon nanotube (CNT) yarn muscles containing PSS are denoted "PSS@CNT" herein). FIG. 1G is a high resolution transmission electron microscope (HR-TEM) image of the CNT yarn surface after infiltrating with PSS, which shows a multiwall nanotube that has a layer of PSS.

FIG. 2A is an illustration of the stroke changes that occur in going from positive voltages to negative voltages for a neat, coiled CNT yarn muscle, and the stroke changes for an unipolar-stroke yarn muscle during the same voltage changes. FIG. 2B illustrates the structure changes of a PSS@CNT muscle when actuated in 0.1 M LiCl aqueous electrolyte. In contrast with ordinary electrochemical muscles (like pristine CNT yarn), which increase volume and therefore contract when the potential is either increased or decreased from near zero voltage (vs Ag/AgCl), the PSS@CNT muscle monotonically increases volume and monotonically contracts in length upon decreasing voltage from +1V to −1V (vs Ag/Ag/Cl). FIG. 2C is a graph showing tensile actuation versus time for electrochemical actuation of a two-ply, a coiled PSS@CNT yarn and a neat, two-ply, coiled yarn in response to an applied square wave potential. FIG. 2D is a graph showing the dependence of tensile actuation on applied square wave potential for a two-ply, coiled PSS@CNT and a two-ply, coiled, neat CNT yarn.

FIG. 3A is a graph showing a cyclic voltammetry scan of a coiled pristine CNT yarn electrode in an electrolyte during sinusoidal stretch, and during the same scan without deformation. FIG. 3B is a graph showing cyclic voltammetry of a coiled PSS@CNT yarn electrode in an electrolyte during the same conditions as FIG. 3A. FIG. 3C is a graph showing tensile actuation of neat, two-ply, coiled CNT yarn driven by cyclic voltammetry. FIG. 3D is a graph showing tensile actuation of a two-ply, coiled, PSS@CNT yarn driven by cyclic voltammetry. FIG. 3E is a graph showing the time dependence of tensile actuation for a neat CNT yarn during cyclic voltammetry. FIG. 3F is a graph showing the time dependence of tensile actuation for the unipolar stroke PSS@CNT muscle during cyclic voltammetry.

FIG. 6A is a graph showing tensile stroke and capacitance versus potential scan rate for a two-ply, coiled PSS@CNT muscle and a two-ply, coiled, neat CNT muscle during cyclic voltammetry, versus an Ag/AgCl reference. The inset shows CV curves of neat CNT muscle and PSS@CNT muscle under the same scan rate. FIGS. 6B-6D are graphs showing the frequency dependence of tensile stroke for different applied potential waveforms ((FIG. 6B) sine wave, (FIG. 6C) square wave, and (FIG. 6D) cyclic voltammetry (triangle wave)) for PSS@CNT and neat CNT two-ply, coiled yarn muscles in different electrolytes.

FIG. 8A is a graph showing tensile stroke, as a percent of the loaded muscle length, versus applied stress for isobaric actuation for pure CNT yarn, PSS@CNT yarn, and PSS@CNT/PDDA@CNT yarn that were coiled by twist insertion. (Dual-electrode yarn muscles containing PSS@CNT as one electrode and PDDA@CNT as the opposite electrode are designated as "PSS@CNT/PDDA@CNT" muscles herein.) FIG. 8B is a graph showing the results of FIG. 8A when normalized to the initial non-loaded muscle length. The inset schematic diagrams are for neat, coiled CNT yarn; PSS@CNT yarn; and PSS@CNT/PDDA@CNT yarn. FIG. 8C is a graph showing the contractile work of the actuator (FIG. 8A) produced by a square wave potential (versus Ag/AgCl reference), compared against other actuator technologies. The inset shows tensile stroke versus cycle number for a coiled PSS@CNT yarn, when excited by a square-wave voltage with lifting an applied load. FIG. 8D is a chart that identifies the symbols in FIG. 8C.

FIGS. 9A-9B are graphs of the dependence of current and the amplitude of current change, respectively, on the applied potential for pure CNT. FIGS. 9C-9D are graphs of the dependence of current and the amplitude of current change, respectively, on the applied potential for CTAB modified-CNT. FIGS. 9E-9F are graphs of the dependence of current and the amplitude of current change, respectively, on the applied potential for rGO/PEDOT:PSS and CTAB bi-modified CNT FIGS. 9G-9H are graphs of the dependence of current and the amplitude of current change, respectively, on the applied potential for P-doped CNT.

DETAILED DESCRIPTION

The present invention provides carbon nanotube yarn artificial muscles in which muscle stroke increases or decreases monotonically with increase of potential, thereby enabling a total stroke that is a non-cancelling sum of anodic and cathodic strokes. These muscles are referred to herein as "unipolar-stroke artificial muscles", since their behavior contrasts with previous electrochemical carbon nanotube (CNT) muscles, whose stroke direction changes in going from extreme negative potentials to positive potentials. The believed mechanism of this unipolar-stroke behavior, as well as optimizing it by tuning the potential of zero charge (pzc), is explained herein. A wide variety of unipolar stroke artificial muscles can be effectively achieved by this means, such as by biscrolling ionic polymer or conducting agents, and by modification via yarn surface functionalization.

As used herein, the term "yarn" includes yarns, fibers, and filaments. As used herein, the term "monotonic potential range" refers to the potential range over which a yarn monotonically increases or monotonically decreases actuator stroke during increase in potential. As used herein, the term "monotonic potential range fraction" refers to the potential range over which the yarn monotonically increases or monotonically decreases actuator stroke during increase in potential, divided by total potential range over which the actuator can be actuated without electrochemical degradation.

Yarn Fabrication and Morphology

The fabrication process of ~200-μm-diameter unipolar muscle is as follows. CNT sheets were first drawn from a multiwalled carbon nanotube (MWNT) forest [Zhang 2004], assembled into 2-cm-wide, 7-cm-long sheet stacks containing ~70 layers, and supported vertically on a metal frame. An aqueous solution of polyelectrolyte, either poly(sodium 4-styrenesulfonate) (PSS) or poly(diallyldimethylammonium chloride) (PDDA) was deposited by dip infiltrating on both sides of the sheet stack to ensure uniform infiltrating of the hydrophobic CNT bundles. (Poly(sodium 4-styrenesulfonate) (PSS) and poly(diallyldimethylammonium chloride) (PDDA) are used in experimental demonstration of invention embodiments). In some instances, a surfactant (such as Triton X-100) was optionally used in the deposited solution. After drying in air at room temperature, the sheet stack was vertically suspended between rigid supports, which were then attached at the top to a motor and at the bottom to a 20 g load.

Figure 1F:
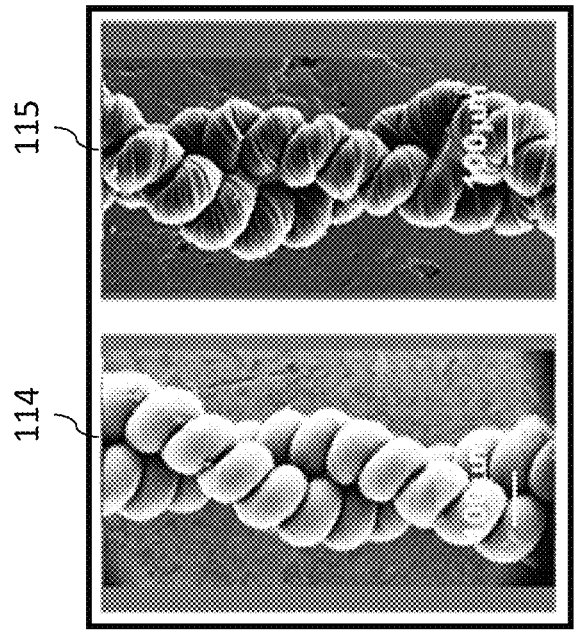
Figure 1G:
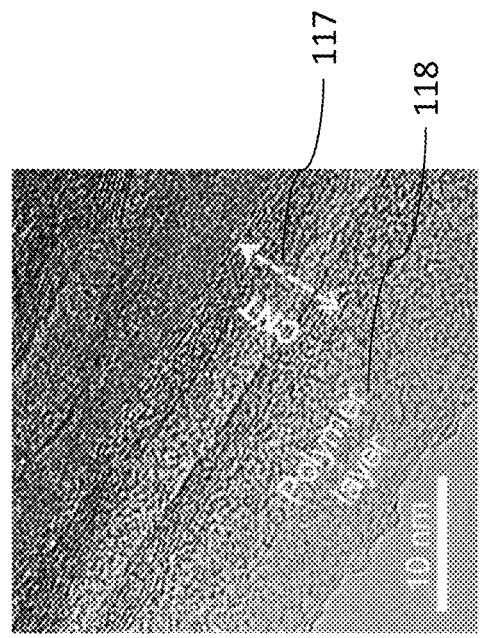
Figure 1E:
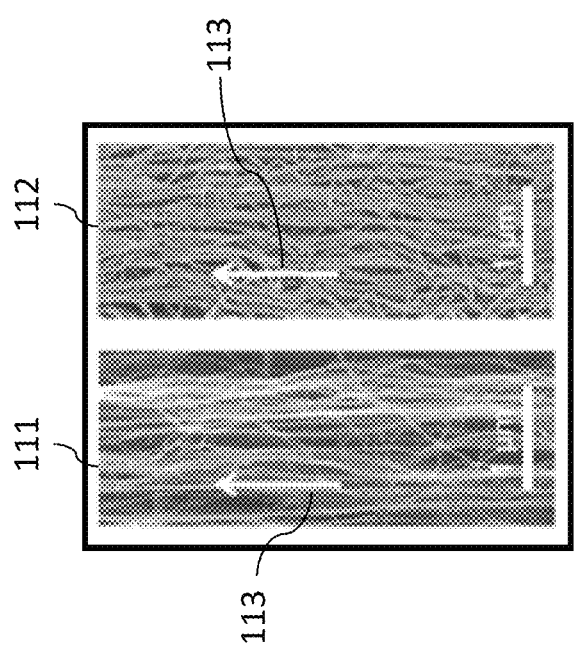

While preventing the bottom from rotating, the yarn was twisted either to just before the onset of yarn coiling or to a twist level that caused complete coiling (FIG. 1A). FIG. 1A shows schematic illustrations (from left to right) of the pristine CNT sheet 101, the CNT sheet infiltrated by polyelectrolyte 102, and twist insertion 103 into this infiltrated sheet to make either twisted yarns 104 or twisted and coiled yarns 105. The term coiled yarn is used to indicate yarns that are both twisted and coiled. The amount of inserted twist to make twisted yarns and fully coiled yarns was ~3,800 turns/m and ~4,200 turns/m, respectively. FIGS. 1B-1D illustrate, respectively the structures of twisted yarns 106, coiled yarns 107, and two-ply coiled yarns 108. The pictured top 109 red and bottom 110 yarn-end attachments are tethers, which prevent end rotation. Microscopic morphologies of the neat and infiltrated CNT sheets, yarns, and bundles are detailed in FIGS. 1E-1G. FIG. 1E shows SEM images of an aligned neat CNT sheet before polyelectrolyte infiltrating (SEM image 111) and a PSS infiltrated CNT sheet (SEM image 112), where the arrows 113 indicate the alignment directions of the CNTs in these two sheets. FIG. 1F shows SEM images of a two-ply coiled CNT yarn 114 and a coiled PSS@CNT yarn 115. FIG. 1G is a HR-TEM image of the CNT yarn surface after infiltration with PSS, which shows a multi-wall nanotube 117 that has a layer of PSS 118.

The nanotubes in the twisted yarn provide a bias angle α (the angle between the yarn length direction and nanotube alignment direction) of approximately $$\alpha = \tan^{-1}(2\pi rT), \quad (1)$$

where r is the distance from the yarn center and T is the amount of inserted twist per twisted yarn length.

The bias angle on the yarn surface is measured by scanning electron microscope (SEM) imaging. Over-twisting the CNT yarn results in coiling, which greatly amplifies tensile stroke and specific work as compared to those for uncoiled yarn.

Actuator Performance and Mechanism

The reported work capacities and power densities are values during muscle contraction. For an optimized step-potential change, the full-cycle power density is the contractile work-per-cycle divided by the cycle time and the maximum average power density is the ratio of contractile work to actuation time for an optimized time. The reference electrodes for potential in aqueous and organic electrolytes were Ag/AgCl and platinum, respectively. Here and elsewhere, except for two electrode solid-state muscles, a large capacitance counter electrode (a CNT-covered Pt mesh) was used and tensile actuation was characterized under constant load (isobaric condition) while the yarn was torsionally tethered. Unless otherwise indicated, for fairly comparing, unipolar and bipolar actuation, the performance metrics of bipolar muscles includes only potential ranges where stroke cancellation does not occur.

A twisted or coiled PSS or PDDA infiltrated CNT yarn and a counter electrode (platinum mesh and high surface area carbon material) are immersed in an electrolyte. Applying a voltage between working and counter electrodes causes actuation. Although only two electrodes were needed to produce tensile actuation, a reference electrode (Ag/AgCl) was used to measure the potential of the actuating yarn. For tensile actuation measurements, the yarn was tethered at both ends to prohibit irreversible yarn untwist. Actuation was measured under constant tensile load, and is reported normalized to the loaded muscle length.

Figure 2A:
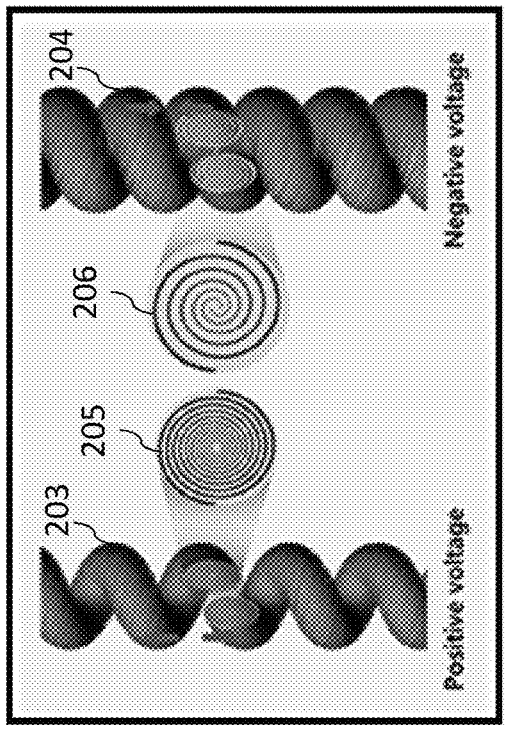
FIGS. 2A-2D show unipolar-stroke artificial muscles.
Figure 2B:
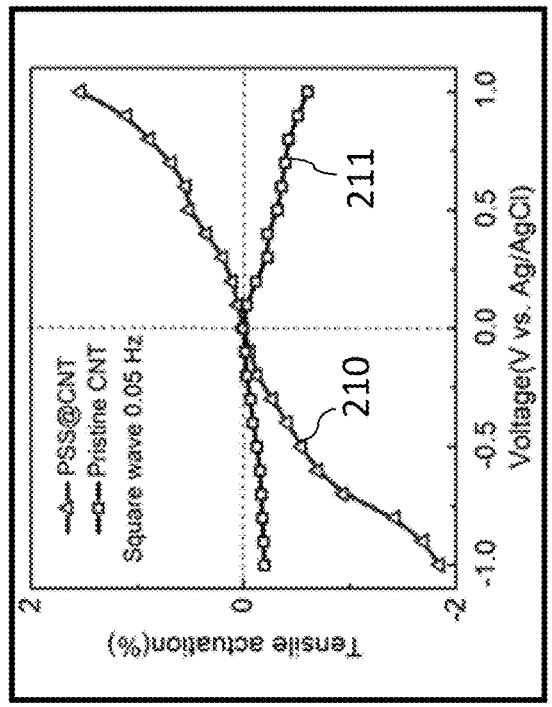
Figure 2C:
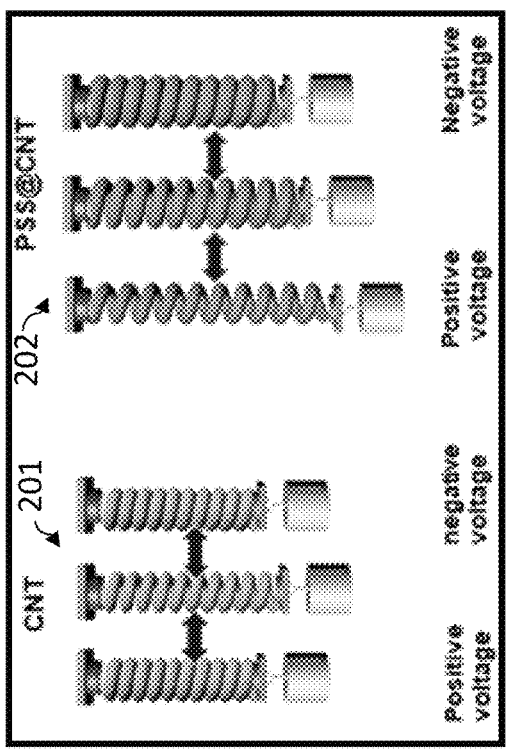
Figure 2D:
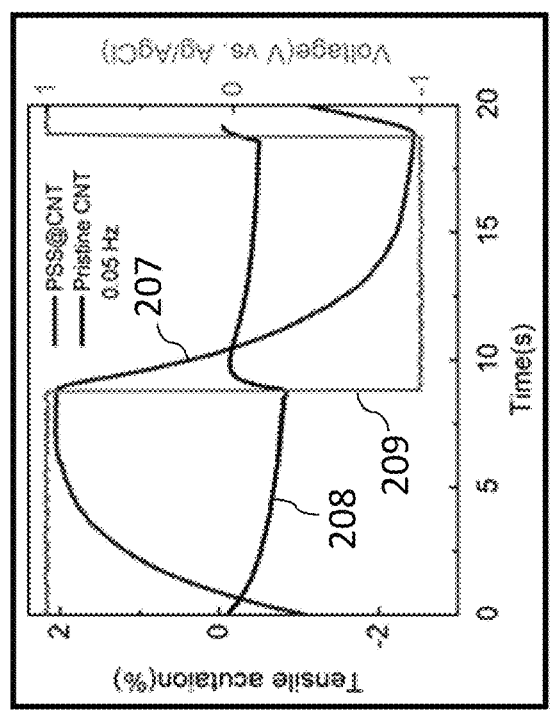

FIG. 2A is an illustration of the stroke changes that occur in going from positive voltages to negative voltages for a neat, coiled CNT yarn muscle 201, and the stroke changes for an unipolar-stroke yarn muscle 202 during the same voltage changes. FIG. 2B is an illustration of the structure of a PSS@CNT muscle during actuation in 0.1 M LiCl aqueous electrolyte. On going from extreme positive potentials (203) to extreme negative potentials 204, vs Ag/AgCl, the muscle's length monotonically contracts as the muscle diameter monotonically expands due to injection of hydrated $Li^+$ ions (insets 205 and 206). FIG. 2C is a graph showing tensile actuation versus time for electrochemical actuation of a two-ply, coiled PSS@CNT yarn (plot 207) and a neat, two-ply, coiled yarn (plot 208) in response to an applied 0.05 Hz square wave potential of +/−1 V (plot 209). FIG. 2D is a graph showing the dependence of tensile actuation on applied 0.05 Hz square wave potential for a two-ply, coiled PSS@CNT (plot 210) and for a two-ply, coiled, neat CNT yarn (plot 211). The applied stress was 14.2 MPa in FIGS. 2C-2D.

To generate large actuation strokes, previous electrochemically-driven, neat CNT yarn artificial muscles rely on organic electrolytes to take advantage of both large ion size and high driving voltages [Lee 2017]. The lack of large electrochemical windows and typically smaller ion sizes for aqueous electrolytes usually results in very small strokes and work capabilities for neat CNT yarn artificial muscles. Furthermore, as in previous work, both negative potentials and positive potentials caused neat CNT yarns to contract (FIG. 2C, plot 208), because of yarn volume expansion due to the absorption of solvated cations and anions, respectively.

FIG. 2C-2D shows the experimentally-observed unipolar-stroke behavior of a two-ply, coiled, PSS-infiltrated CNT yarn muscle (PSS@CNT) (plot 207 and 210, respectively), where strokes at both negative and positive potentials additively contribute to the total stroke. As a result, a stroke of ~5% was obtained (plot 207), which is ~6 times that observed (plot 208) for a two-ply, coiled neat CNT yarn (FIG. 2C).

In order to understand the origin of this unusual unipolar-stroke behavior, piezoelectrochemical spectroscopy (PECS) was used to determine the potential of zero charge (pzc) of the PSS@CNT muscle [Kim 2017]. During PECS, a cyclic tensile strain is applied during a conventional cyclic voltammetry (CV) scan in order to probe the charge density on the yarn. The potential of zero charge is the potential at which the amplitude of stretch-induced current changes becomes zero, because a stretch-induced capacitance change will only produce a varying current if there is charge on the electrode.

Figure 3A:
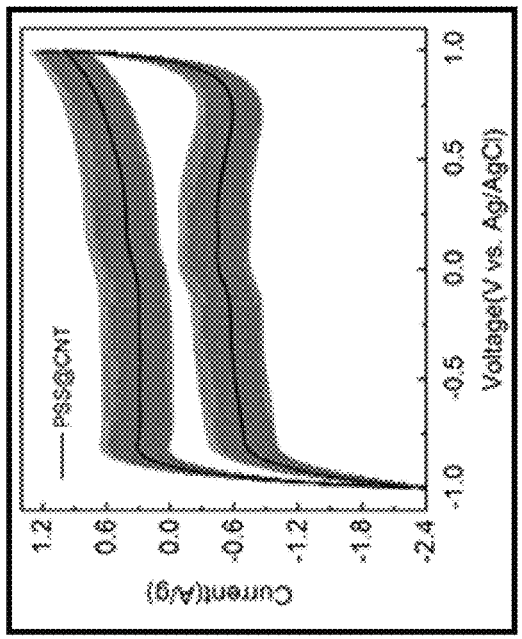
FIGS. 3A-3F show measurements relating to actuation mechanism and actuator stroke for neat coiled artificial muscles and coiled unipolar-stroke muscles.
Figure 3B:
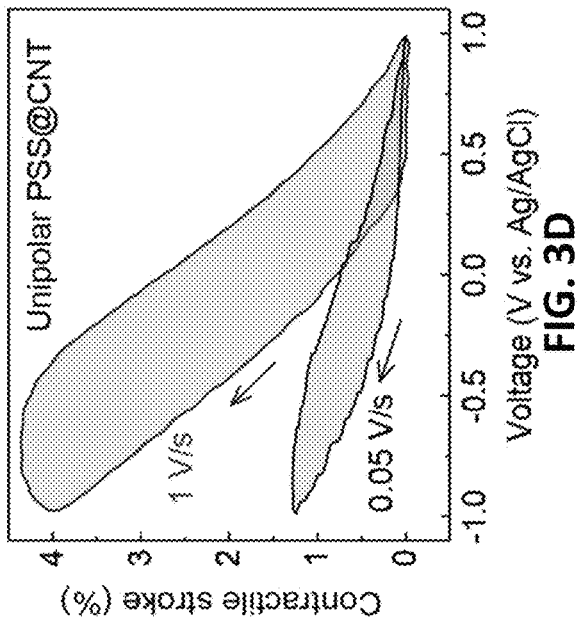
Figure 3C:
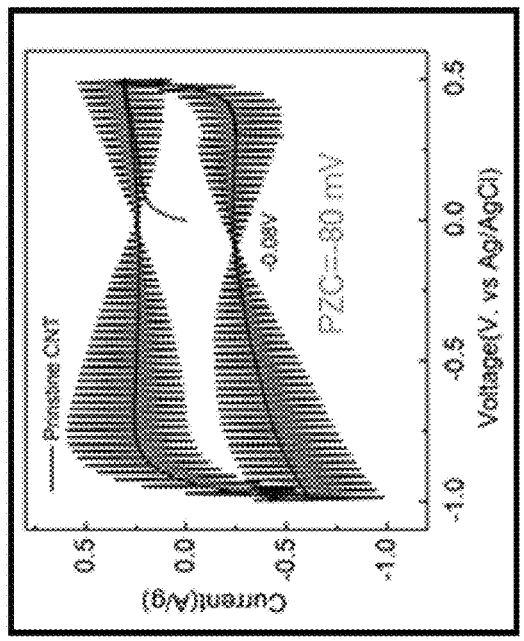
Figure 3D:
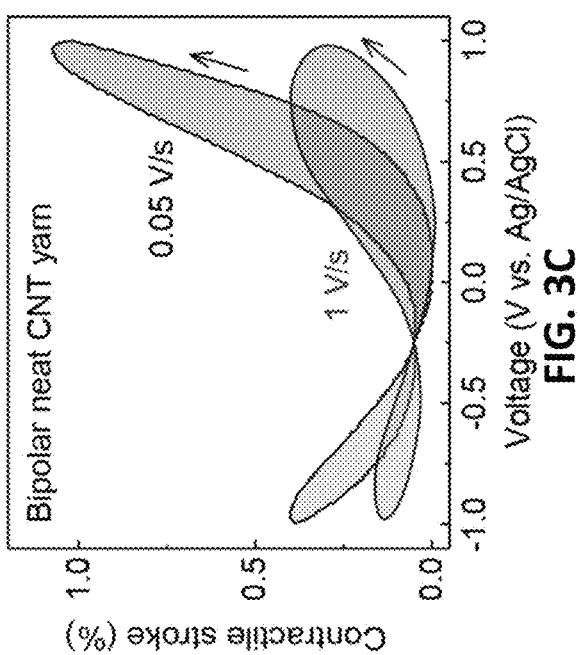
Figure 3E:
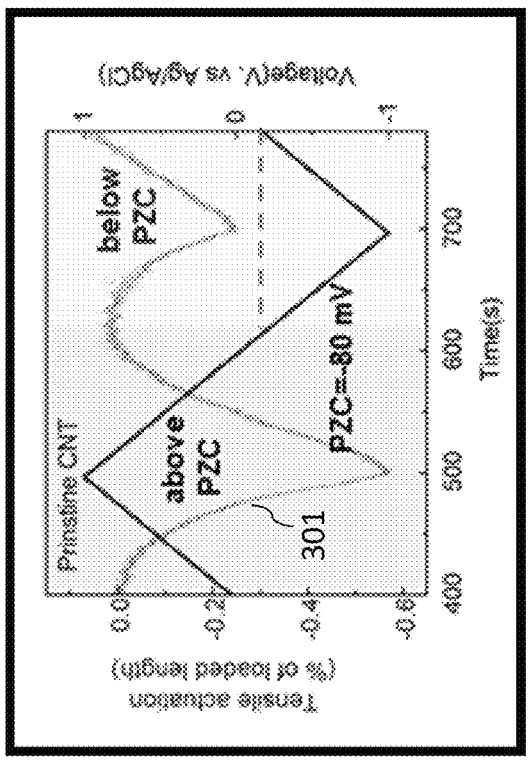
Figure 3F:
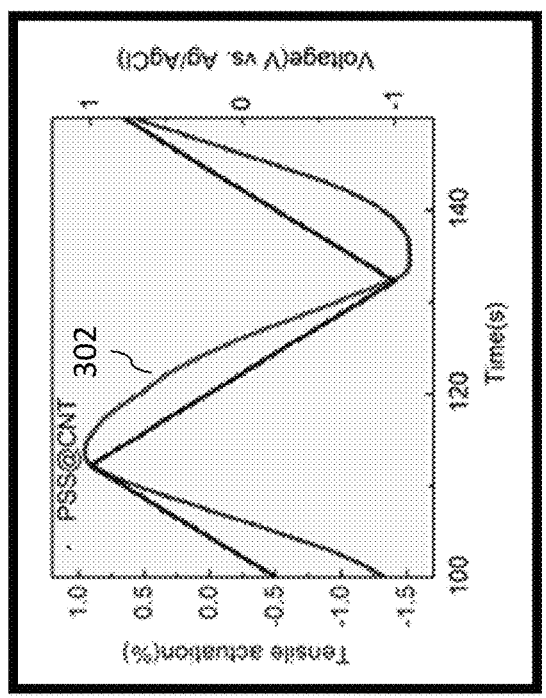

FIG. 3A is a graph showing cyclic voltammetry (50 mV/s scan rate) of a coiled pristine CNT yarn electrode in 0.1 M LiCl during 5 Hz sinusoidal stretch to 10%, and during the same scan without deformation. FIG. 3B is a graph showing cyclic voltammetry (50 mV/s scan rate) of a coiled PSS@CNT yarn electrode in 0.1 M LiCl during the same conditions as FIG. 3A. FIG. 3C is a graph showing tensile actuation of neat, two-ply, coiled CNT yarn driven by cyclic voltammetry (at 0.05 V/s and 1 V/s scan rates), where the injected ion switches from $Li^+$ to $Cl^-$ on opposite sides of the potential of zero charge (pzc=−80 mV). FIG. 3D is a graph showing tensile actuation of a two-ply, coiled, PSS@CNT yarn driven by cyclic voltammetry (at 0.05 V/s and 1 V/s scan rates), where only solvated $Li^+$ ions are injected and removed at all potentials due to the shifted pzc (above the +1 V stability limit of the electrolyte). FIG. 3E is a graph showing the time dependence of tensile actuation for the neat CNT yarn (plot 301) during cyclic voltammetry at 10 mV/s. The two contractile actuation peaks occur for injection of $Li^+$ ions at negative potentials and $Cl^-$ ions at positive potentials, relative to the pzc. FIG. 3F is a graph showing the time dependence of tensile actuation for the unipolar stroke of single-ply coiled PSS@CNT muscle (plot 302) during cyclic voltammetry at 100 mV/s. Only $Li^+$ ions participate due to the shifted pzc, providing a contractile muscle stroke that monotonically increases as potential is scanned from +1 V to −1V (vs Ag/AgCl) and monotonically decreases when the direction of potential scan is reversed.

The surprising result, shown in FIG. 3B, is that the pzc of PSS@CNT is so positive (above 1 V vs. Ag/AgCl) that it is outside of the electrochemical stability window of the aqueous electrolyte, when operated in 0.1 M LiCl. In contrast, the pzc of the neat CNT yarn (FIG. 3A) is near 0 V with respect to the Ag/AgCl reference electrode in the same electrolyte. This means that cations are injected into the PSS@CNT yarn over the entire potential window, while the range of cation injection for the neat CNT yarn is restricted by the fact that the pzc falls near the middle of the potential window. Hence, the potential range over which the cations are injected for the PSS@CNT yarn is much broader than for the neat CNT yarn. This results in the much larger observed stroke for the PSS@CNT yarn when scanning from negative potentials to positive potentials versus Ag/AgCl. FIGS. 3C-3F show the tensile stroke and ionic species that drive this tensile stroke during triangle-wave CV scans. Note that the stroke behavior versus applied potential for PSS@CNT yarn is unipolar, while that for the neat CNT yarn is bipolar. Hence, the muscle stroke is much larger for the PSS@CNT yarn than for the neat CNT yarn. This stroke for the PSS@CNT yarn can be dramatically increased by optimization of the content of PSS, and the potential scan rate.

Figure 4:
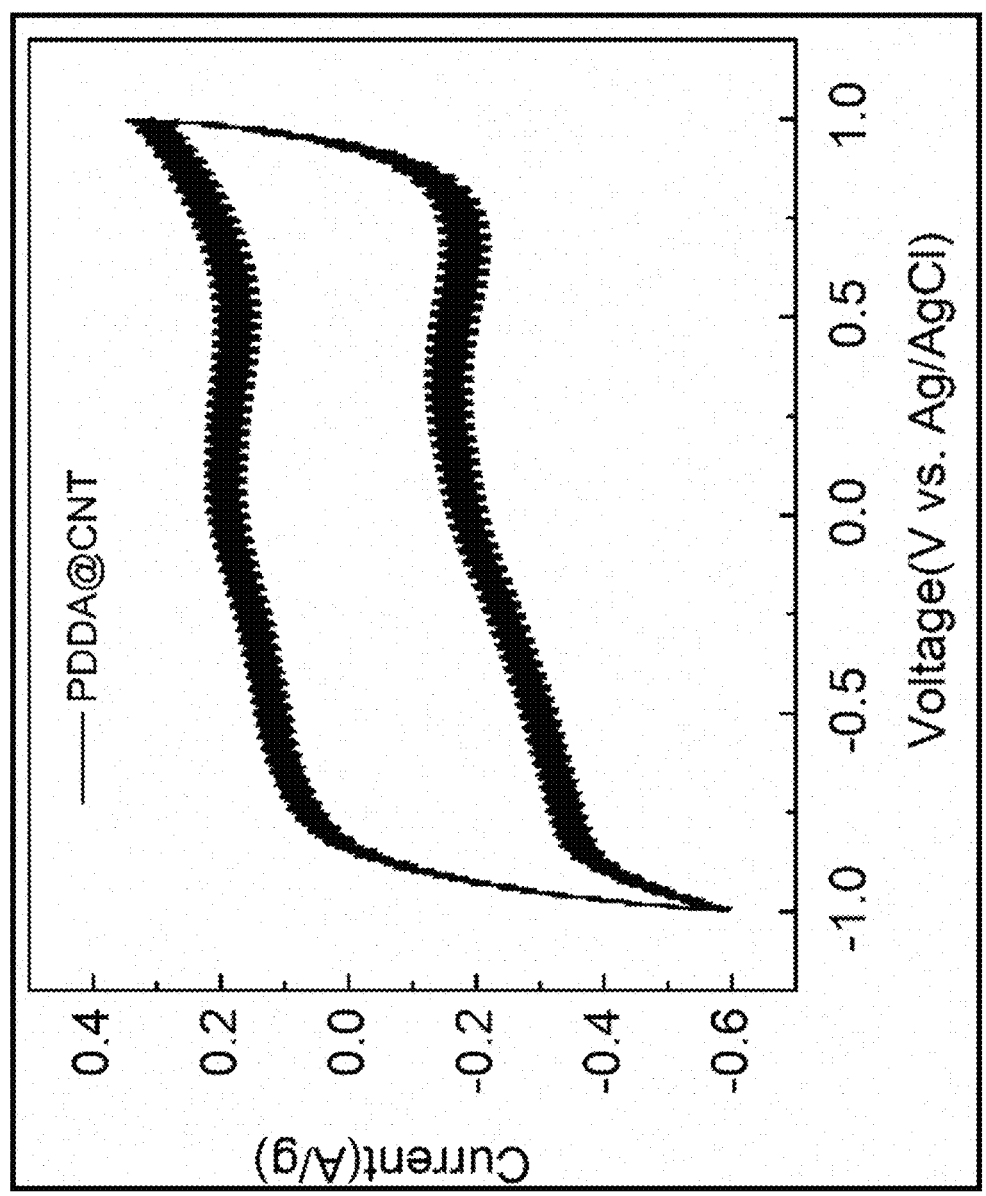
FIG. 4 is a graph showing cyclic voltammetry during sinusoidal stretching to determine the potential of zero charge (pzc) of a coiled PDDA@CNT yarn in an electrolyte (Carbon nanotube (CNT) yarn muscles containing PDDA are denoted "PDDA@CNT" herein).).
Figure 5B:
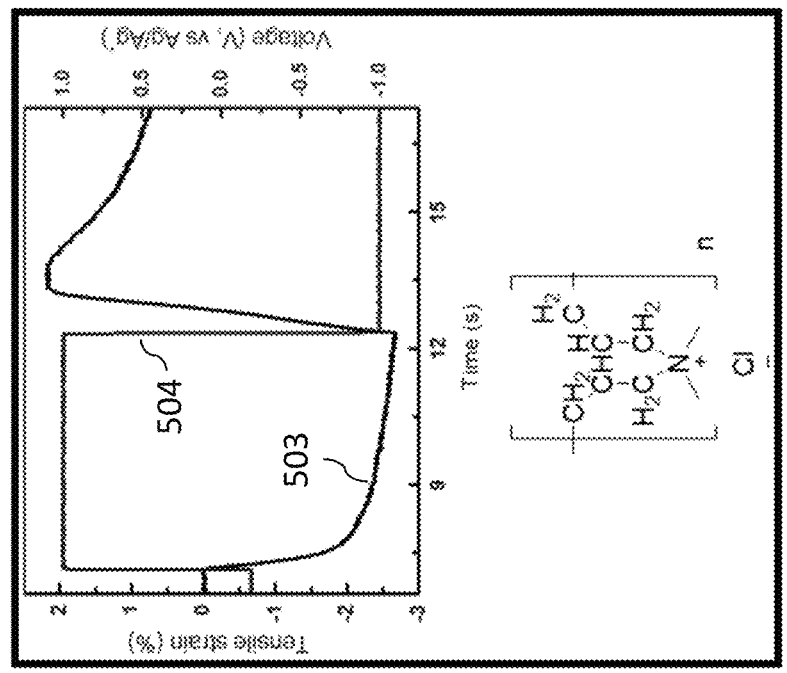
FIGS. 5A-5B are graphs showing tensile actuation strain versus time during square-wave actuation of (FIG. 5A) a coiled PSS@CNT yarn and (FIG. 5B) a coiled PDDA@CNT yarn.
Figure 5A:
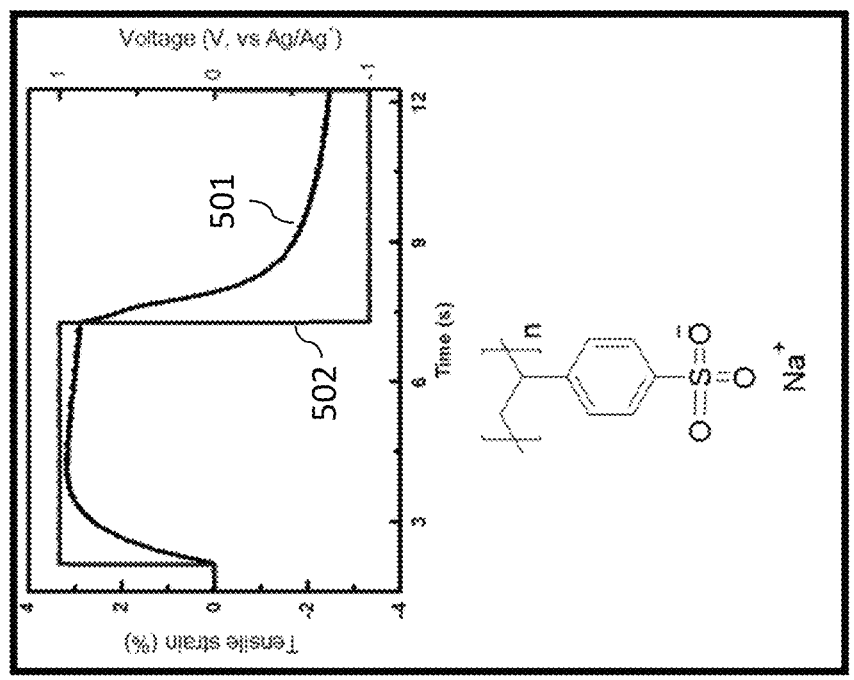

FIG. 4 shows cyclic voltammetry during sinusoidal stretching to determine the pzc of a coiled PDDA@CNT yarn in 0.1 M LiCl electrolyte. These results indicate that the pzc is below −1.0 V, which is outside the electrochemical stability window of this electrolyte. FIG. 5 shows that the PDDA@CNT yarn provides similar unipolar stroke behavior as does PSS@CNT yarn. However, there is an important difference. Since the PDDA contains positively-charged bound groups, while the PSS contains negatively-charged bound groups, the pzc of the PDDA@CNT yarn is shifted in the opposite direction as for PSS@CNT yarn (to below −1 V vs. Ag/AgCl for PDDA@CNT, and to above +1 V vs. Ag/AgCl for PSS@CNT), as shown in FIG. 3B and FIG. 4. Consequently, unipolar stroke behavior is obtained for both yarns, although the direction of voltage-dependent tensile stroke is opposite for these yarns. This difference results since anions are inserted and removed during an actuation cycle for PDDA@CNT, whereas cations are inserted and removed during an actuation cycle for PSS@CNT. FIGS. 5A-5B shows tensile actuation strain versus time (plots 501 and 503, respectively) during 0.1 Hz square-wave actuation (plots 502 and 504, respectively) of coiled (FIG. 5A) PSS@CNT yarn and (FIG. 5B) PDDA@CNT yarn. These results show that changing the potential (vs. Ag/AgCl) from 1 V to −1 V provides a contractile stroke of −5.2% for PSS@CNT and a stroke in the reverse direction of +4.8% for PDDA@CNT.

Figure 6B:
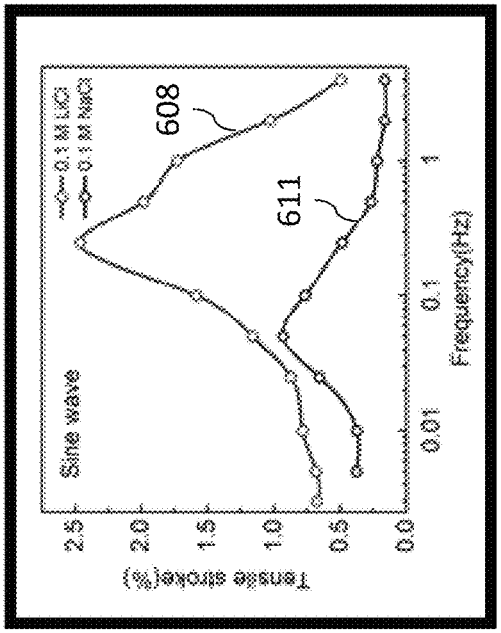
FIGS. 6A-6D show the anomalous rate dependence of muscle stroke.
Figure 6D:
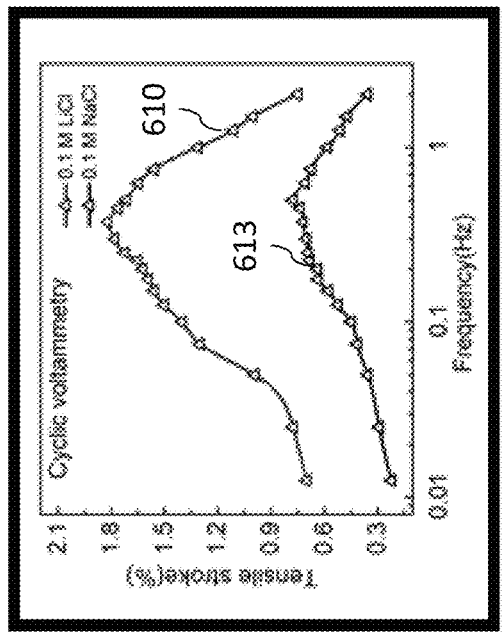
Figure 6A:
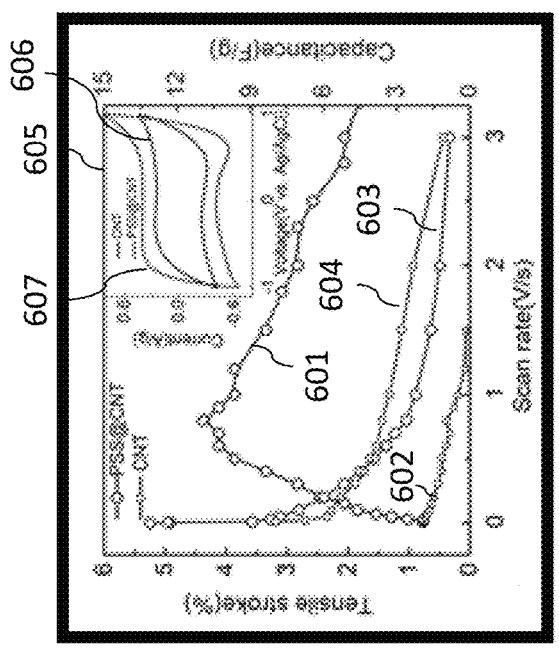

In contrast to results obtained for other electrochemical CNT muscles, it was surprisingly observed that the stroke of the two-ply, coiled PSS@CNT yarn first increases with increasing potential scan rate, and then shows the expected decrease of stroke with further increase in scan rate (FIG. 6A). This increase in muscle stroke with increasing scan rate is called scan rate enhanced stroke (SRES). In contrast to this behavior, the two-ply, coiled neat CNT yarn shows the normal decrease of muscle stroke with increasing potential scan rate (FIG. 6A). Furthermore, both neat CNT and PSS@CNT yarns show the expected decrease in capacitance with increasing potential scan rate (FIG. 6A).

FIG. 6A shows tensile stroke and capacitance versus potential scan rate for a two-ply, coiled PSS@CNT muscle (plot 601 for tensile stroke and plot 603 for capacitance) and a two-ply, coiled, neat CNT muscle (plot 602 for tensile stroke and plot 604 for capacitance) during cyclic voltammetry, versus an Ag/AgCl reference. The inset 605 shows CV curves at 100 mV/s (plots 606-607 for the two-ply, coiled PSS@CNT muscle and CNT muscle, respectively). The tensile stroke for the neat CNT yarn monotonically decreases as the scan rate increases, while the tensile stroke for the PSS@CNT yarn initially increases with increasing scan rate and reaches a peak stroke amplitude at an 800 mV/s scan rate. The capacitance of both decreases with the increase of scan rate.

Ion injection to compensate injected negative charge can be either by cation insertion or anion removal, or a combination thereof. This possibility is not an explanation for the strange scan rate dependence that is observed for the PSS@CNT muscle, since PSS transports only cations, and in fact is often used in fuel cells and water treatment columns as a cation exchange material. The possible alternative explanation is that time-dependent processes are occurring due to changes in the degree of cation hydration or electroosmotic drag; relaxation in polymer chain structure, volume, or hydration; or a combination thereof.

The maximum tensile actuation versus scan rate is shown in FIG. 6A for triangle wave voltage scans. The stroke of the two-ply, coiled, neat CNT yarn (~3,780 turns/m of inserted twist) decreases as the scan rate increases. This is understandable, since the amount of double layer charge injection depends on the yarn's capacitance, and the yarn capacitance decreases with increasing scan rate. As shown in FIG. 6A, at the lowest scan rate (10 mV/s), the stroke of the coiled, neat CNT yarn (0.81%) is comparable to that of the two-ply, coiled PSS@CNT yarn (0.77%).

Figure 6C:
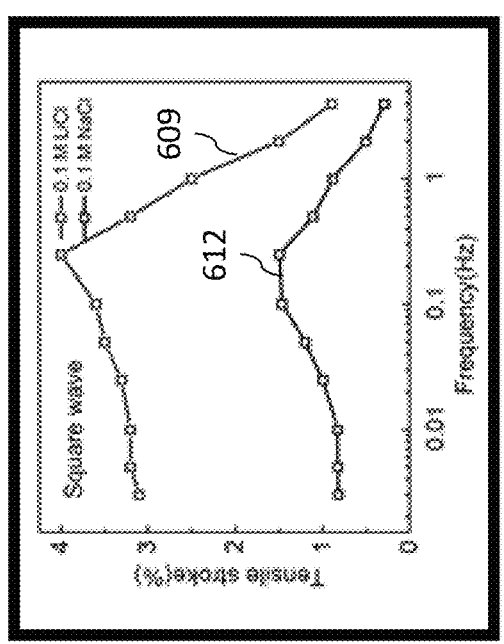

Most importantly, for frequencies below 0.2 Hz, the tensile actuation of the PSS@CNT yarn increases with increasing scan rate for the triangle wave voltage scans, even though the capacitance of both this yarn and the neat CNT yarn monotonically decrease with increasing scan rate. FIGS. 6B-6D compare the scan rate dependence of muscle stroke for a PSS@CNT yarn in 0.1 M LiCl and 0.1 M NaCl electrolytes during sine wave, square wave, and triangle wave voltage scans. Plots 608-610 are the respective plots for 0.1 M LiCl, and plots 611-613 are the respective plots for 0.1 M NaCl. Note that in all cases the stroke increases with increasing frequency until a peak is obtained, and then decreases. Likewise, the stroke obtained in 0.1 M LiCl is higher than in 0.1 M NaCl. This increased stroke for the LiCl electrolyte can be partially, but incompletely, explained by the larger volume of solvated Li$^+$ (233 Å$^3$) than for solvated Na$^+$ (192 Å$^3$) [Nightingale 1959].

The difference in the results of FIGS. 6A and 6D is due to a difference in the weight fraction of PSS infiltrated into the yarn, and the applied tensile load during actuation. The weight fraction of PSS, relative to the total yarn weight, is 51 wt. % for the yarn of FIG. 6A, versus 23 wt. % for the yarn of FIGS. 6B-6D. The applied load was 16.8 MPa and 12.1 MPa for FIG. 6A and FIGS. 6B-6D, respectively, when normalized to the cross-sectional area of the twisted yarn before actuation, rather than the cross-sectional area of the coiled muscle. Unless otherwise indicated, this normalization of stress will be used.

Figure 7:
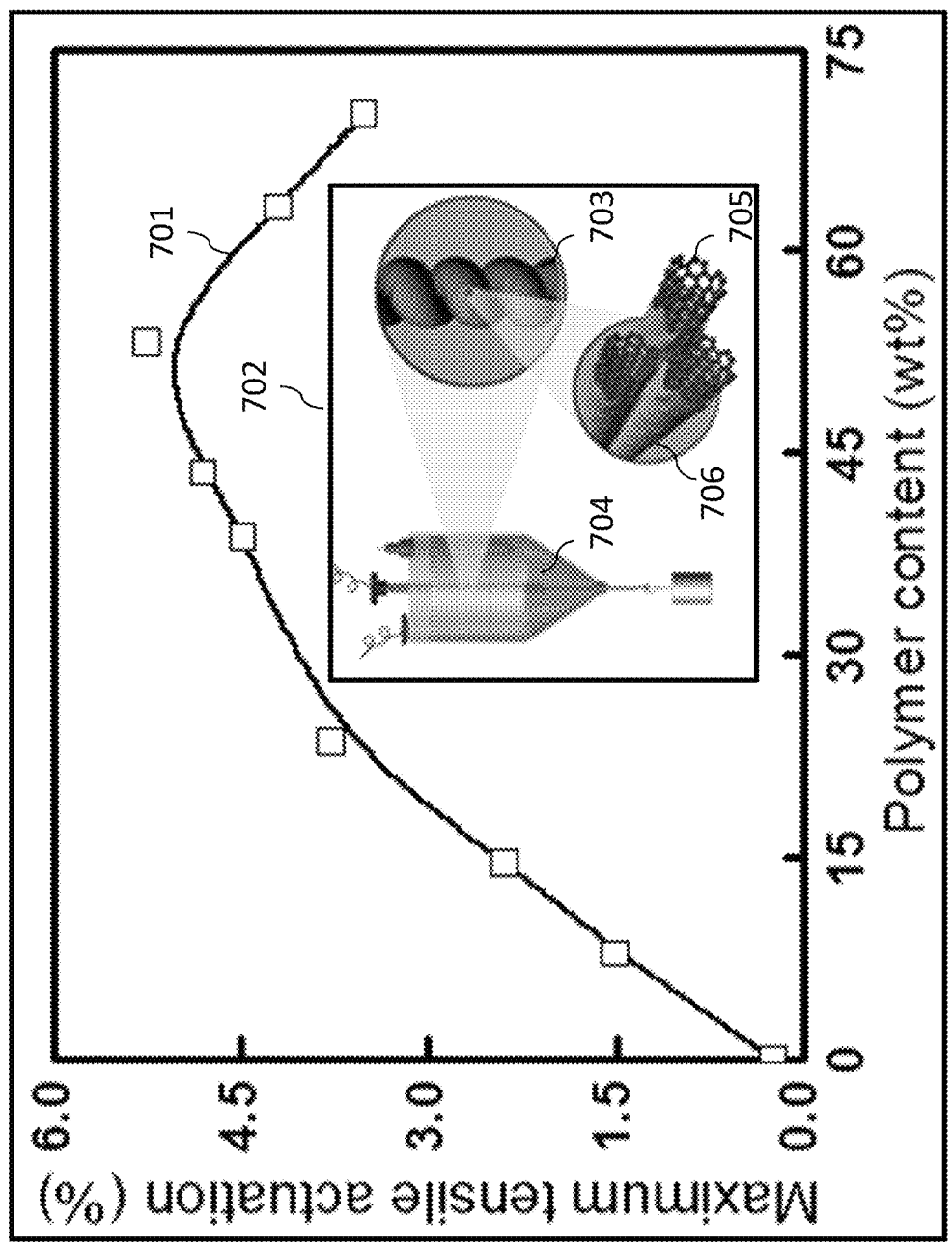
FIG. 7 is a graph showing the relationship between the maximum tensile stroke and the weight percent of PSS polyelectrolyte in a coiled PSS@CNT yarn (measured by thermal gravimetric analysis). The inset depicts a muscle electrode isobarically actuating in an electrolyte, as well as the relationship between the nanotubes in the yarn and the polyelectrolyte layer.

FIG. 7 shows that the tensile stroke depends upon the weight of infiltrated polyelectrolyte, with respect to the total yarn weight. In fact, tensile stroke is maximized for a much higher weight concentration of polyelectrolyte than needed for coating the nanotubes with an electrochemical-double-layer thickness of polymer. On the other hand, too high a weight of polyelectrolyte acts to restrict the volume change due to the volume change of the double layer. Thus, PSS concentrations above ~60 wt. % result in a decrease in tensile stroke (FIG. 7). Plot 701 of FIG. 7 shows the relationship between the maximum tensile stroke and the weight percent of PSS polyelectrolyte in a coiled PSS@CNT yarn (measured by thermal gravimetric analysis). These strokes were measured in 0.1 M LiCl aqueous electrolyte. The inset 702 depicts a muscle electrode 703 isobarically actuating in an electrolyte 704, as well as the relationship between the nanotubes 705 in the yarn and the polyelectrolyte layer 706.

Since the polyanionic polymer PSS and the polycationic polymer PDDA have opposite charges fixed on polymer chains, oppositely charged ions are injected and removed from the PSS@CNT and PDDA@CNT yarn when the applied voltage is changing. Therefore, as a consequence of having the actuation of both anode and cathode yarns in the same direction, PSS@CNT and PDDA@CNT yarns can be mechanically coupled to provide a single fiber that utilizes the stroke contributions of both electrodes. By infiltrating these separated yarn pairs with a gel electrolyte (0.5 M aqueous LiCl in cellulose) to enable inter-electrode ion transport, an all-solid-state electrochemical muscle was realized (FIG. 8B). This elimination of the need for an electrolyte bath is important for most practical applications.

Figure 8A:
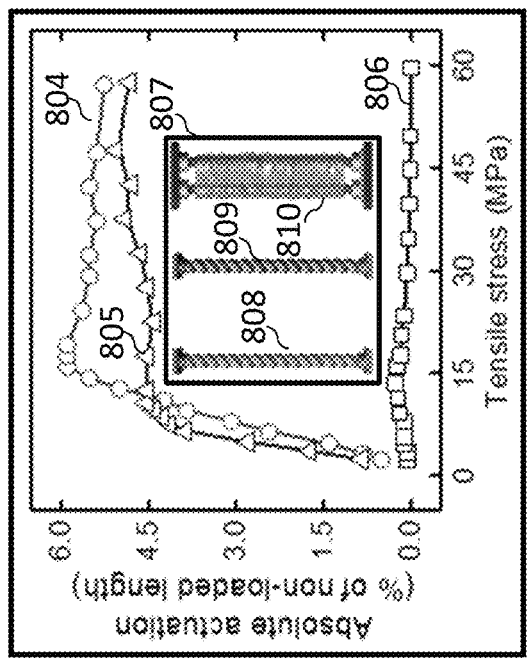
FIGS. 8A-8D show coiled muscle stroke, specific work capacity, and specific power capacity.
Figure 8B:
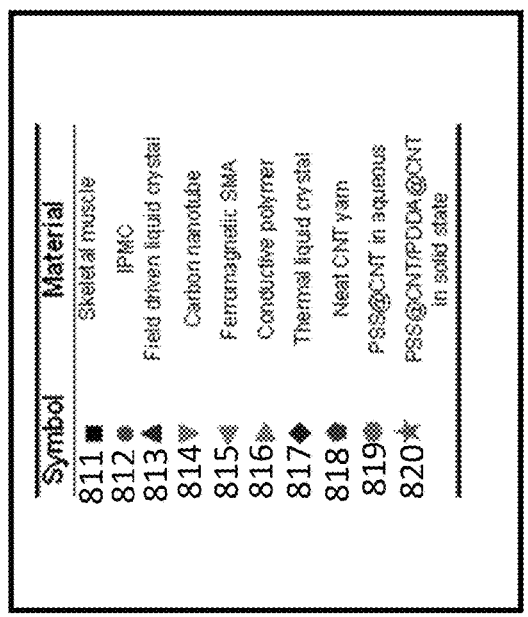

FIG. 8A shows tensile stroke, as a percent of the loaded muscle length, versus applied stress, for isobaric actuation for pure CNT yarn (diameter d=177 μm) (plot 801), PSS@CNT yarn (diameter d=174 μm) (plot 802), and PSS@CNT/PDDA@CNT yarn (diameter d=148 μm) (plot 803), where the actuating electrodes were coiled by inserting 4,220 turns/m of twist. The electrolyte for the neat CNT and PSS@CNT yarn muscles was 0.1 M LiCl aqueous electrolyte, while the electrolyte for the PSS@CNT/PDDA@CNT was a 0.5 M LiCl aqueous electrolyte cellulose gel, solid electrolyte. FIG. 8A plots the load dependence of tensile stroke for a neat, coiled CNT muscle and a PSS@CNT coiled muscle in aqueous electrolyte, and for the dual-electrode, gel-electrolyte-infiltrated PSS@CNT/PDDA@CNT muscle. The total stroke is the maximum stroke that can be obtained by scanning from one potential extreme to the other extreme within the bounds of the electrochemical stability window. For low applied stresses, inter-coil contact limits muscle contraction. Hence, muscle stroke increases with increasing load until a maximum value is realized. For the neat, coiled CNT yarn (left illustration 808 of inset 807 in FIG. 8B), the maximum stroke (0.24%) occurred for an optimal load of 13.6 MPa. For the PSS@CNT yarn muscle, the maximum stroke (obtained for the optimal load of 15.9 MPa) was 5.21%, which is ~22 times the maximum stroke of the pure CNT yarn. The all-solid-state, dual-electrode PSS@CNT/PDDA@CNT muscle provided a maximum stroke of 3.85% at an optimal load of 12.5 MPa.

FIG. 8B shows the results of FIG. 8A when normalized to the initial non-loaded muscle length (plots 804-806 corresponding to plots 801-803, respectively), indicating that the absolute displacement during tensile actuation remains nearly constant at loads above that providing maximum stroke in FIG. 8A. The inset 807 shows schematic diagrams are for neat, coiled CNT yarn 808; PSS@CNT yarn 809; and PSS@CNT/PDDA@CNT yarn 810.

The results of FIG. 8B show the muscle stroke that is obtained when normalization is with respect to the length of the non-loaded muscle, which is most useful for calculating the specific work these muscles generate during contraction. Note that the resulting absolute displacements reach approximate plateaus for loads at which inter-coil contact does not occur. Therefore, specific contractile work approximately linearly increases with applied load over this plateau region until loads at which the muscle fails.

Figure 8C:
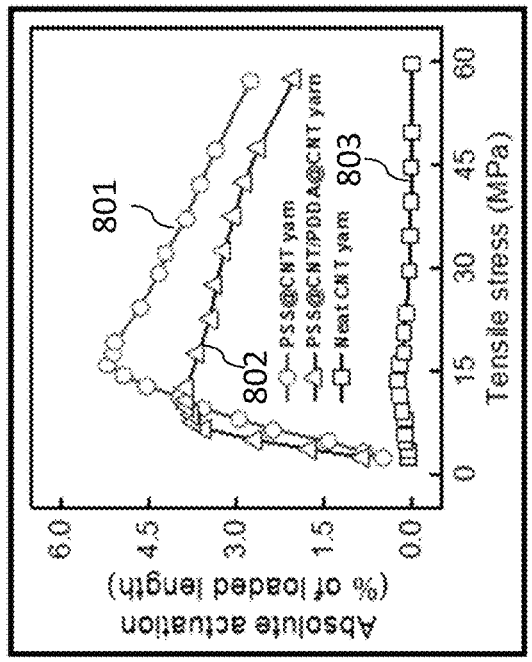
Figure 8D:
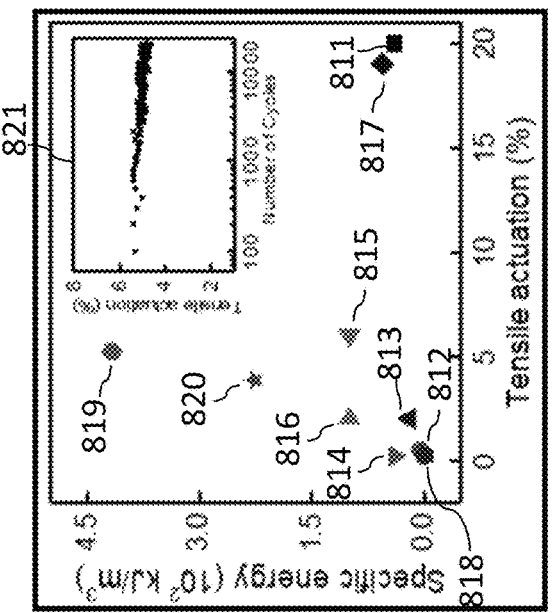

FIGS. 8C-8D compare the contractile mechanical work densities and tensile strokes of the present unipolar stroke muscles with previous results for other types of muscles. FIG. 8C shows the contractile work of the actuator (pure CNT yarn 818 (diameter d=177 μm), PSS@CNT yarn 819 (diameter d=174 μm), and PSS@CNT/PDDA@CNT yarn 820 (diameter d=148 μm) as discussed above for FIG. 8A) produced by a 0.1 Hz, ±1 V square wave potential (versus Ag/AgCl reference), compared against other actuator technologies including skeletal muscle 811 [Hunter B 1992], ionic polymer metal composites (IPMCs) 812 [Nemat-Nasser 2003], filed driven liquid crystal 813, carbon nanotube 814 [Baughman 1999; Barisci 2000; Barisci 2003], ferromagnetic SMA 815 [Tickle 1999; Murray 2000; Sozinov 2002], conductive polymer 816 [Baughman 1996; Madden 2002; Bay 2003], and thermal liquid crystal 817 [Thompsen 2001; Finkelmann 2002; Shenoy 2002]. The inset 821 shows tensile stroke versus cycle number for a 9.6-mm-long, coiled PSS@CNT yarn (154 μm diameter and 4,370 turns/m inserted twist), when excited by a 0.1 Hz, square-wave voltage while the applied load was 11.2 MPa. Each point on the graph is the stroke measurement obtained every 100 cycles. FIG. 8D is a chart that identifies the symbols in FIG. 8C.

The contractile work density of the neat, coiled CNT yarn muscle in 0.1 M LiCl is only 9.8 kJ/m$^3$, while the maximum work density of the coiled PSS@CNT yarn muscle in this electrolyte reaches 418 kJ/m$^3$, which is about 11 times that for skeletal muscle. The maximum mechanical output power during contraction (1.04 kW/kg) is 4.6 times that for skeletal muscle. For the dual-electrode, gel electrolyte yarn, the contractile work density is 239 kJ/m$^3$, which is at least 6 times that for skeletal muscle.

A unipolar stroke was also obtained when a PSS@CNT muscle was operated in an organic electrolyte, and the resulting increased electrochemical window enabled extremely large strokes and work capacities. The electrolyte was 0.2 M bis(trifluoromethane)sulfonimide lithium (LiTFSI) in dimethyl sulfoxide (DMSO), and the PSS was 30 wt. % of the total muscle weight. This organic electrolyte muscle provided a 2.0-fold SRES, which is the ratio of the peak stroke to the low scan rate stroke. The SRES results from scan-rate-dependent transport of dimethyl sulfoxide from the electrolyte into the yarn muscle. The muscle stroke reached 17.3% for a 23.1 MPa load, and the maximum work capacity was 3.5 J/g at 0.1 Hz. Although a slightly higher previous record exists (3.8 J/g for plied, twist-released CNT yarns), the used scan rate was 20 mV/s, which is seldom practical [Kim 2019]. Increasing the scan rate to 0.5 V/s reduced the work capacity for this previous record-holding muscle to 1.4 J/g, which is far below the 3.32 J/g at this scan rate for the above unipolar stroke muscle. The peak stroke of 18.6% for the unipolar muscle, which occurs at 0.1 Hz for a −3 to 1 V square wave, is reduced to 4.5% at 1 Hz, where the full-cycle contractile power density is 1.4 W/g.

The highest work capacity in an aqueous electrolyte was obtained for unipolar muscles containing Nafion. These muscles were made analogously to the PSS@CNT muscles, by infiltrating 2.5 wt. % nafion in a 1:2 water/ethanol mixture. Like for PSS@CNT, unipolar actuation occurs for nafion@CNT because of a shift of the pzc to above +1 V, which is outside the electrochemical window of the 0.2 M LiCl aqueous electrolyte. SRES also occurs for nafion@CNT and the peak stroke (4.3%) is similar to that for PSS@CNT (4.4%). The contractile work capacity of the nafion@CNT reaches 1.04 J/g, which is 4.4 times the previously record for an electrochemical muscle operating in an aqueous electrolyte [Qiao 2018]. The contractile efficiency was 6.1% for a scan rate of 200 mV/s, which is even higher than the previously reported record in an organic electrolyte (5.4%) [Lee 2017]. To avoid self-discharge, this maximum efficiency was obtained for a voltage range of 0.2 to −1.2 V, where the work capacity and stroke were reduced to 0.4 J/g and 2.5%, respectively.

Note that a unipolar muscle cannot be made by merely inserting a nafion membrane between muscle and counter electrodes that are operated in an aqueous LiCl electrolyte. While the inter-electrode charge transport for both electron and hole injection is exclusively by $Li^+$, $Cl^-$ ions are inserted into the electrochemical double layer during hole injection. Hence, the observed actuation is bipolar and the actuation during electron injection is small, like for the bipolar neat yarn muscle.

A coiled PSS@CNT muscle delivered over 20 thousand cycles during periodic actuation at 0.1 Hz (inset of FIG. 8C), raising and lowering a weight that produced an 11.2 MPa tensile stress. This actuation was driven by applying a ±1 V square wave potential (versus Ag/AgCl reference), and was measured every 100 cycles. The muscle stroke decreased by only about 5.3% of the initial stroke during these 20,000 cycles.

These results show that the stroke of an electrochemically-driven artificial muscle can be dramatically increased by shifting the potential of zero charge of the muscle electrode to either extreme positive or extreme negative values. In this way, unipolar stroke muscles have been obtained, which avoid the issue of stroke cancellation over the electrochemical window of the electrolyte.

Rather than incorporating the material that provides a pzc shift inside the artificial muscle, this material can be incorporated within the sheath of a sheath-run artificial muscle (such as disclosed and taught in J. Mu et al., "Sheath-Run Artificial Muscles," Science 365, 150-155 (2019) ("Mu 2019") and U.S. Patent Appl. Ser. No. 62/846,479, which are incorporated by reference herein). For these sheath-run artificial muscles (SRAMs), a sheath on a twisted or coiled fiber or yarn drives electrochemical actuation. This sheath can be a twisted or coiled layer of CNTs that incorporates the material that provides a pzc shift. This material can optionally be identical to the materials described above for materials that are embedded inside a twisted or coiled yarn muscle. As for the case of yarns containing surface derivatized CNTs, a sheath comprising surface derivatized CNTs can be used to obtain unipolar behavior for SRAMs. Likewise, the same solvating-molecule containing electrolytes can be configured around a SRAM to provide the highly desirable SRES behavior.

Types of Applications

Invention embodiments can be applied to electrochemically-driven unipolar stroke artificial muscle yarns of diverse types, which preferably have specific capacitances of above 0.1 F/g. These yarns can optionally include nanoparticles that are incorporated into the yarn by various means, such as by biscrolling [Lima 2011]. Useful examples of such high-surface-area guests are carbon nanotubes, carbon nanohorns, graphene, fullerenes, activated carbon, carbon black, and combinations thereof. Graphitized nanofibers, which can be obtained by pyrolyzing electrospun polymers, like polyacrylonitrile [Kim 2003; Zussman 2005], provide an attractive alternative material to carbon nanotubes for use in unipolar stroke muscles, since they can be spun to below 100 nm diameters and be modified by conventional surface treatments to provide the electrochemical properties needed for these muscles.

The realization of unipolar stroke muscles usefully depends on the ability to provide a shift in the potential of zero charge for the actuating elements within the yarn muscle. The above examples demonstrate the use of a layer of polyanionic polymer PSS or polycationic polymer PDDA to shift the pzc to large positive or large negative potentials, respectively. More generally, this layer can be selected from charge-carrying materials such as a positively-charged amino groups, positively-charged nitrogen-containing groups, positively-charged sulfur-containing groups, positively-charged metal-containing groups, negatively-charged sulfonate groups, negatively-charged carboxyl groups, negatively-charged phosphate groups, and combinations thereof. These functional groups can be contained in a polymer or other inorganic or organic layer that is non-covalently bonded to the actuating yarn or an actuating component thereof, or can directly be partially or fully covalently attached, directly or indirectly, to the actuating yarn or an actuating component thereof. Ion-exchange materials such as used for cation-conducting membranes and anion-conducting membranes are especially preferred for use in shifting the pzc towards more positive and more negative potentials, respectively.

Such a shift in pzc can also result from partially or fully covalently attaching materials to the actuating yarn, or actuating components thereof, wherein said covalently attached material is selected from a group consisting of oxygen, nitrogen, boron, sulfur, and combinations thereof.

A unipolar stroke was also observed for CNT yarns that were coated with a surfactant, sodium dodecyl sulfate (SDS). These yarns were prepared by absorbing SDS on a low twist density yarn and washing away excess SDS using deionized water, before inserting twist to provide complete coiling. The pzc is shifted positively to beyond the electrochemical window of the used 0.2 M LiCl aqueous electrolyte. Together with unipolar stroke behavior, SRES was observed. A peak muscle contraction of 2.8% was obtained for a scan rate of 1.1 V/s, while the muscle contraction at a low scan rate (20 mV/s) was only 35.7% of this value, and similar to that for the neat CNT yarn in this electrolyte. Hence, hydrated $Li^+$ and bare $Li^+$ produce actuation at high and low potential scan rates, respectively. The observed work capacity for square wave excitation reached 0.79 J/g and the maximum average power density during contraction and the full-cycle average contractile power density were 2.7 and 2.0 W/g, respectively. The stroke at 1 Hz was an impressive 2.7%, and was 4.0% at 0.1 Hz. Even though the surfactant is soluble in the electrolyte, over 8,000 nearly reversible actuation cycles were observed. Adding 0.6 wt. % surfactant to the electrolyte doubled cycle life.

We also made unipolar muscles by biscrolling graphene oxide (GO) into a CNT yarn. During biscrolling, a guest-coated CNT sheet stack is twist inserted, so that the guest is trapped in the helical corridors of the yarn (Lima 2011). An organic electrolyte (0.2 M $TBA.PF_6$ in acetonitrile, where TBA is tetrabutylammonium) was used. With increasing GO content, the stroke of a CNT yarn muscle gradually changed from bipolar to unipolar, reaching fully unipolar behavior at 25 wt. %. The peak equilibrium tensile contraction and work capacity were 21% and 4.1 J/g, respectively, compared with 16% and 3.2 J/g for the neat yarn in this electrolyte. The contractile stroke of the unipolar GO@CNT muscle at 1 Hz was 8.0%, compared to 2.5% for the neat CNT muscle and the previous 4.7% for a sheath-run CNT muscle at this frequency [Mu 2019]. Also important, the full-cycle contractile power and the maximum average power during contraction were 2.08 and 8.17 W/g, respectively, for the GO@CNT muscle, compared with 1.02 and 2.52 W/g, respectively, for neat CNT yarn muscle. For further comparison, the highest previously reported full-cycle contractile power and maximum contractile average power for operation in an organic electrolyte were 0.99 and 3.71 W/g for a sheath-run artificial muscle and 0.11 and 0.65 W/g for a CNT yarn [Mu 2019].

Figure 9A:
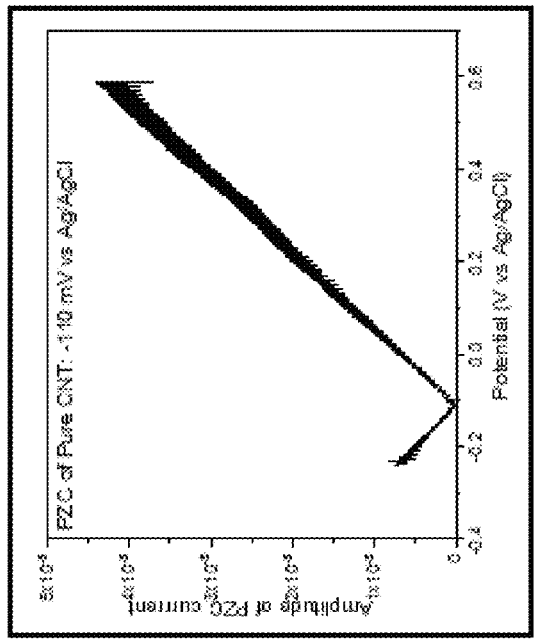
FIGS. 9A-9H are graphs showing the shifting of the potential of zero charge (pzc) for modified CNT yarns.
Figure 9B:
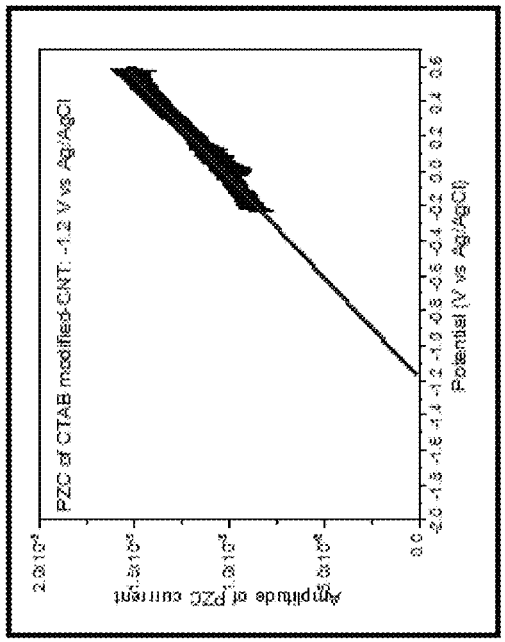
Figure 9C:
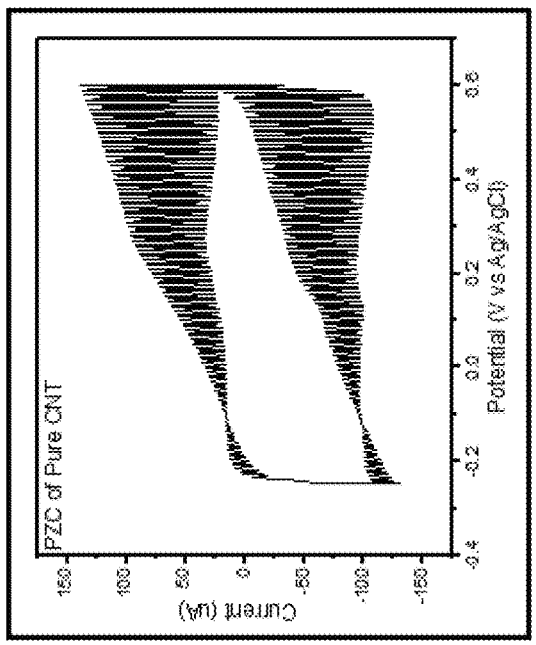
Figure 9D:
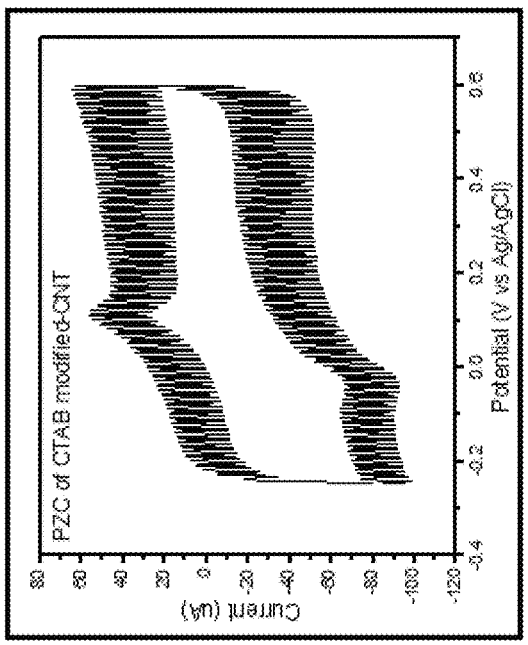

FIGS. 9A-9H are graphs showing potential of zero charge (pzc) shifting for modified CNT yarns in 0.1 M HCl. In this testing, the electrochemical window in the 0.1M HCl was −0.25 to 1V vs. Ag/AgCl. FIGS. 9A-9B are graphs of the dependence of current and the amplitude of current change, respectively, on the applied potential for pure CNT. FIGS. 9C-9D are graphs of the dependence of current and the amplitude of current change, respectively, on the applied potential for CTAB modified-CNT (CTAB, shown in FIG. 10A, is cetyl trimethyl ammonium bromide). For a potential change between −1 to +1 V in 0.1 M LiCl, the maximum observed stroke at a low square wave frequency (0.01 Hz) was 2.8%, the SRES effect was 3-fold, and the stroke at the SRES peak (at 700 mV/s scan rate) was 2.1%.

Figure 9F:
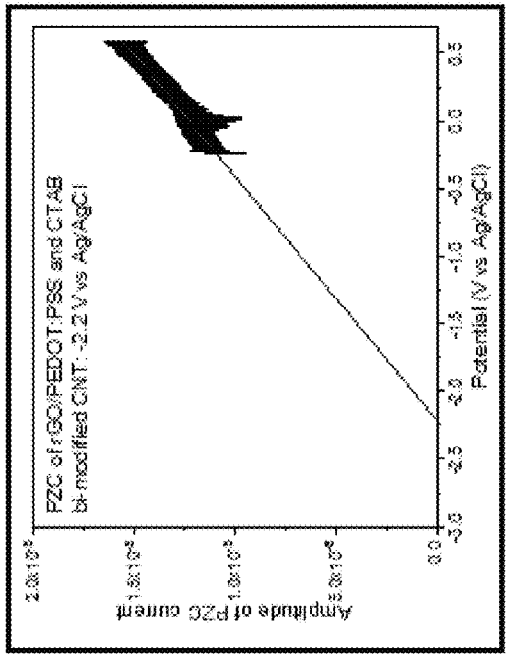
Figure 9H:
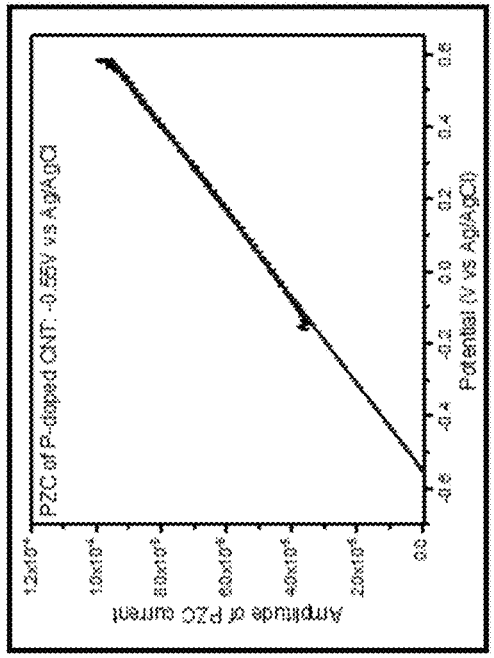
Figure 9E:
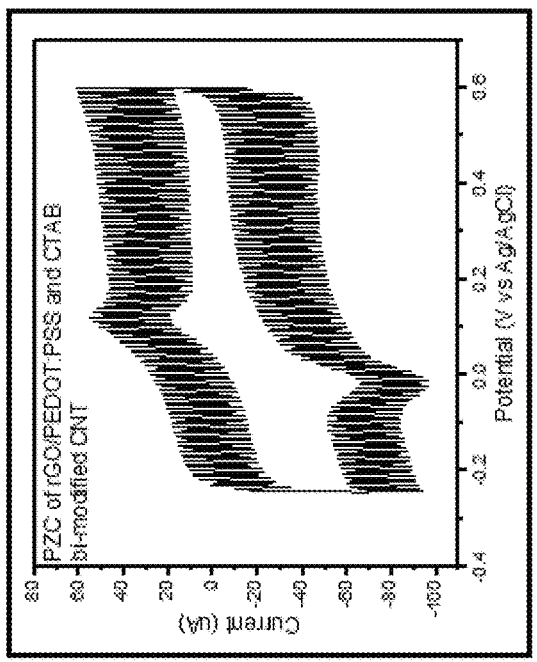
Figure 9G:
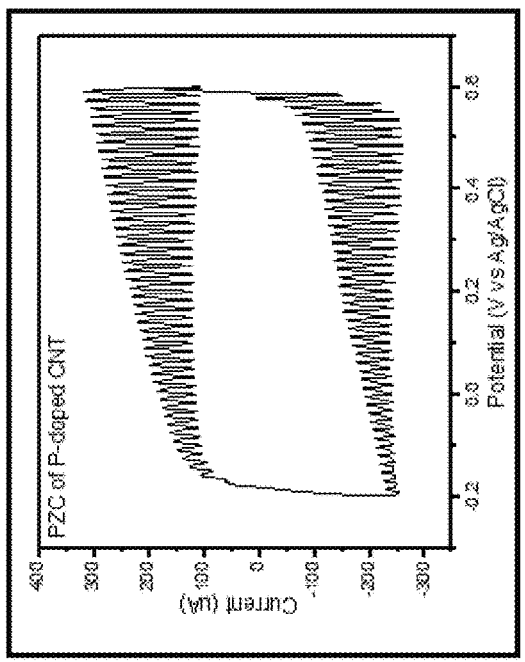
Figure 10B:
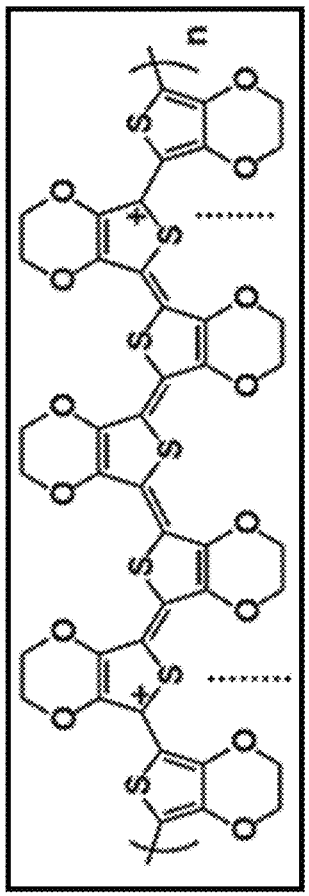
FIGS. 10A-10C are, respectively, illustrations of the CTAB, PEDOT, and PSS utilized for modifying the CNT yarns.
Figure 10A:
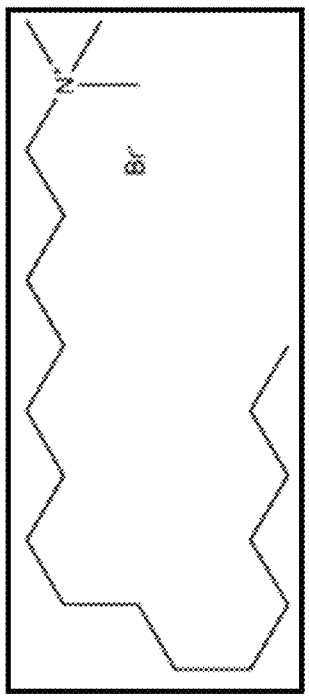
Figure 10C:
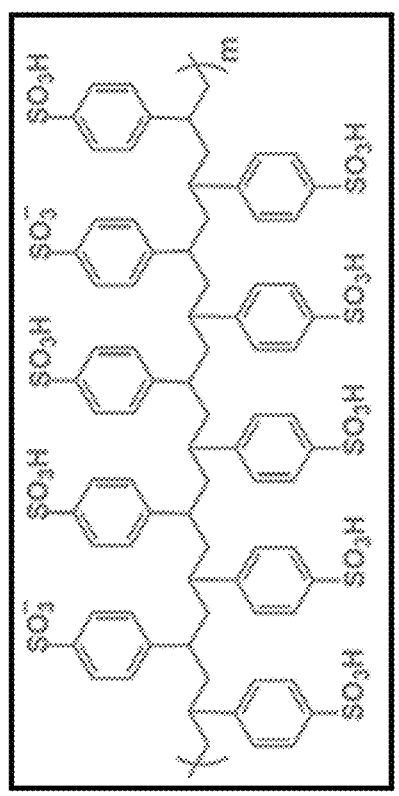
Figure 10D:
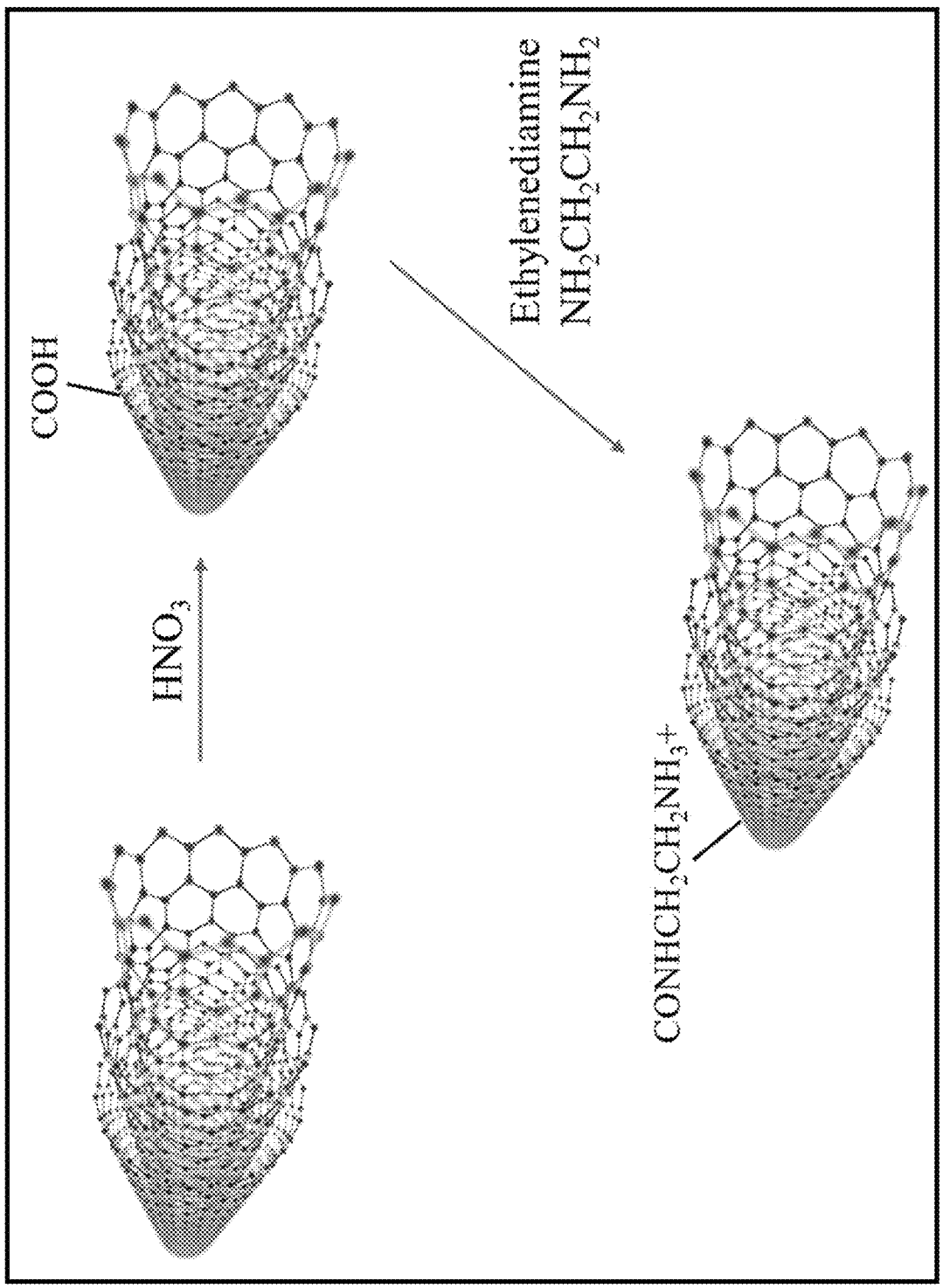
FIG. 10D is an illustration of a carbon nanotube being surfaced doped.

FIGS. 9E-9F are graphs of the dependence of current and the amplitude of current change from PECS measurements, respectively, on the applied potential for rGO/PEDOT:PSS and CTAB bi-modified CNT. (PEDOT and PSS are shown in FIGS. 10B-10C, respectively). FIGS. 9G-9H are graphs of the dependence of current and the amplitude of current change, respectively, on the applied potential for p-doped CNT (with FIG. 10D showing the process by which the carbon nanotubes were surfaced doped).

The utilized electrolytes can be either aqueous or organic and range over the broad spectrum of electrolytes used for batteries, supercapacitors, fuel cells, and other electrochemical applications. Additionally, ionic liquids, and water-in-salt electrolytes can be used as electrolytes. While these alternative electrolytes provide unipolar behavior for PSS@CNT, no SRES was observed. These results indicate the importance of having a solvating species or electrochemically dragged free solvent in the electrolyte that surrounds the actuating muscle.

A main issue for actuation in which muscle stroke results from anion insertion or from cation insertion is the size and mobility of the solvated anion and cation, respectively. Generally, high ion mobilities increase actuation rate and large solvated ion size increases muscle stroke. Especially preferred electrolytes are those comprising ions selected from the group consisting of alkali metal cations, halide anions, tetraalkylammonium cations, $BF_4^-$, $PF_6^-$, bis(trifluoromethanesulfonyl)imide anions, 1-butyl-1-methylpyrrolidinium cations, sulfate anions, and combinations thereof.

Types of modification via yarn surface functionalization can include materials containing bonded charged functionalities selected from the group consisting of a positively-charged amino group, a positively-charged nitrogen-containing group, a positively-charged sulfur-containing group, a positively-charged metal-containing group, a negatively-charged sulfonate group, a negatively-charged carboxyl group, a negatively-charged phosphate group, and combinations thereof.

Figure 11:
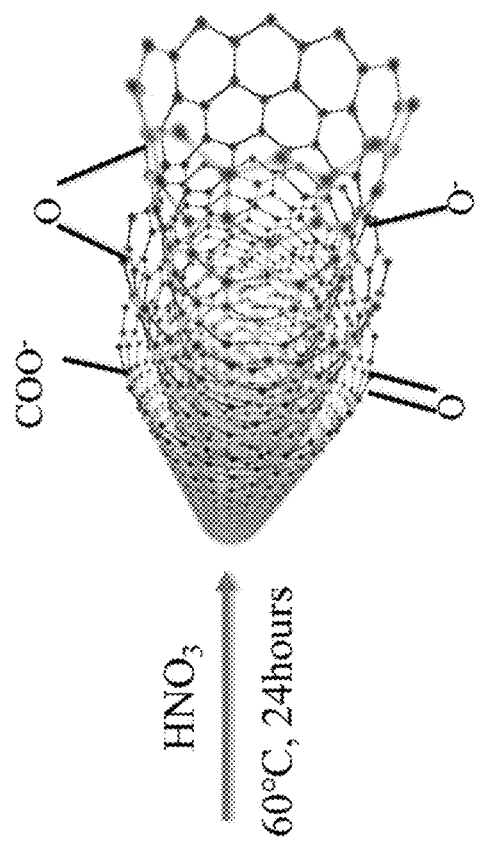
FIG. 11 is an illustration of the derivation of the surface of a nanotube by reaction in nitric acid to produce an n-doped CNT that has a shifted pzc.
Figure 11:
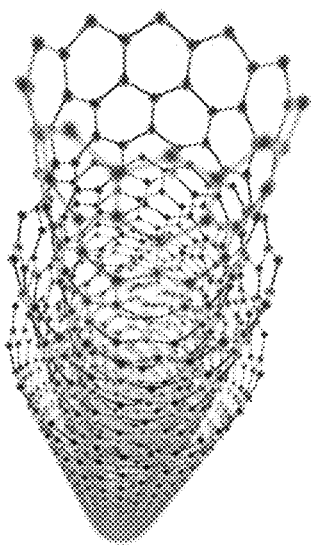

An example of carbon nanotube surface functionalization to shift the potential of zero charge to outside the redox stability range of the electrolyte is next described. As a result of the shift of the pzc, unipolar stroke behavior will be demonstrated for a coiled CNT yarn. To covalently attach negatively-charged functional groups to the surface of a CNT yarn, false-twisted CNT yarn was treated in 6 M $HNO_3$ at 60° C. for 24 hours (FIG. 11). The obtained surface functionalized CNT yarn was then washed several times with DI water and finally dried at room temperature. The yarn was then twisted until it was completely coiled.

Figure 12:
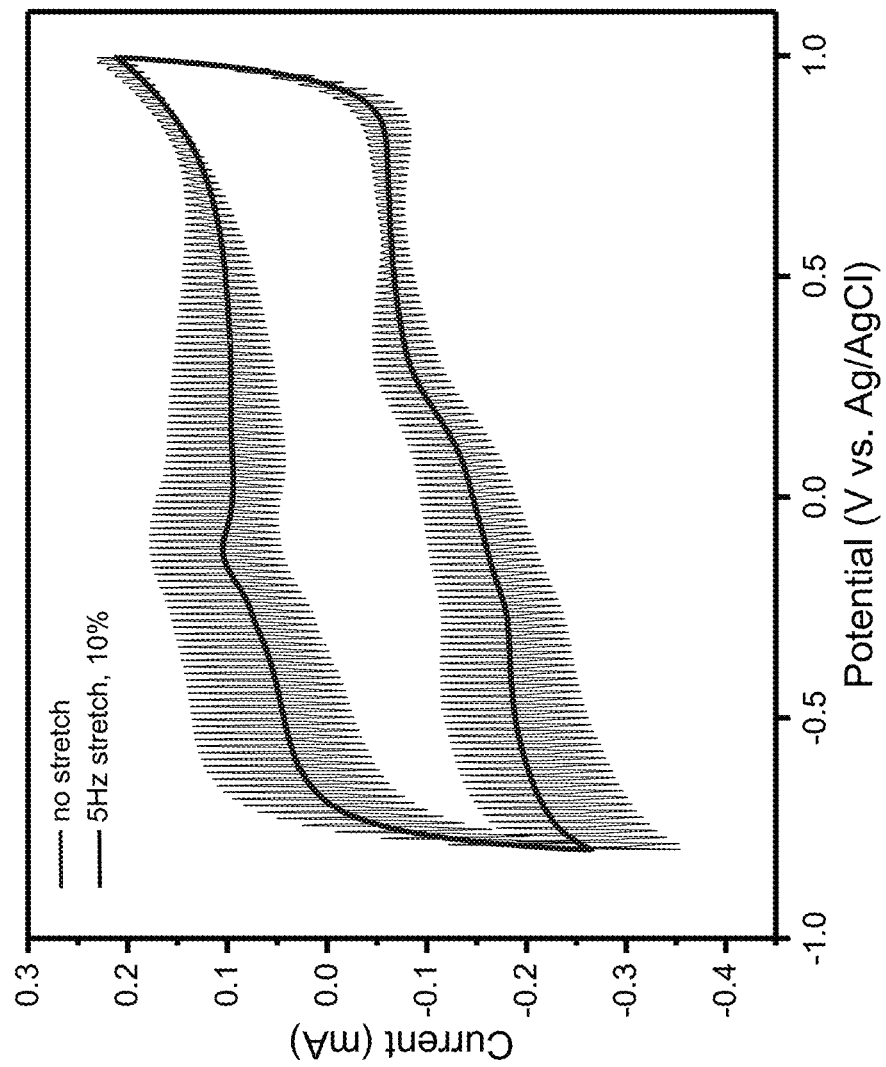
FIG. 12 is a graph showing the results of piezoelectrochemical spectroscopy on the coiled n-doped CNT yarn of FIG. 11, which indicates that the potential of zero charge (pzc) for n-doped CNT yarn has been shifted to outside the redox stability window of the electrolyte.

Cyclic voltammetry (50 mV/s scan rate) during 2 Hz sinusoidal stretch was used to determine the pzc of this coiled yarn in 0.1 M LiCl aqueous electrolyte (FIG. 12). The obtained results shown that the pzc of the functionalized CNT coiled yarn is above 1 V vs. Ag/AgCl, which is outside the electrochemical stability window of the electrolyte. This means that cations are injected into the functionalized CNT coiled yarn over the entire potential window, thereby providing unipolar-stroke behavior.

Figure 13A:
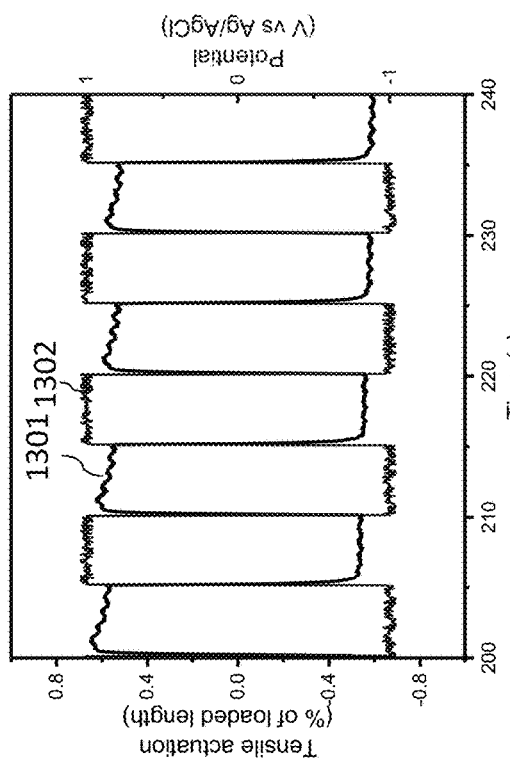
FIGS. 13A-C are graphs showing the time dependence of tensile stroke (lines 1301, 1303, and 1305, respectively), as a percent of loaded muscle length, for different changes in the applied potential (lines 1302, 1304, and 1306, respectively, versus an Ag/AgCl reference electrode) for isobaric actuation of the n-doped coiled CNT yarn of FIG. 11. The potential changes are +1 to −1 V for FIG. 13A, −1 to 0 V for FIG. 13B, and +1 to 0 V for FIG. 13C.
Figure 13C:
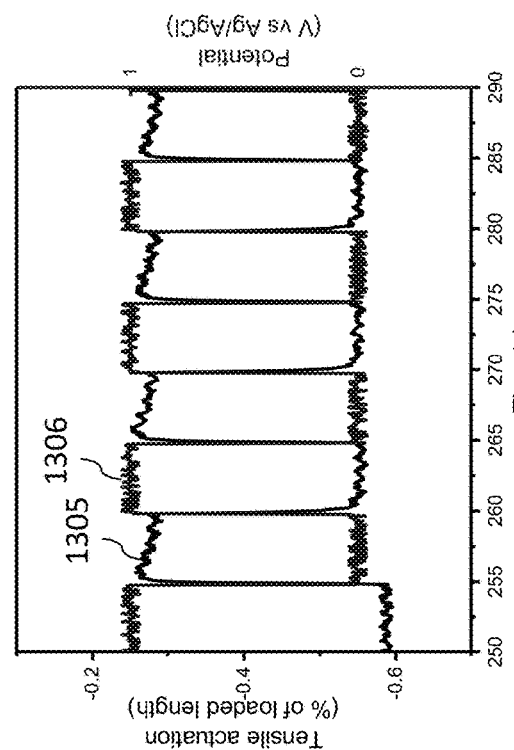
Figure 13B:
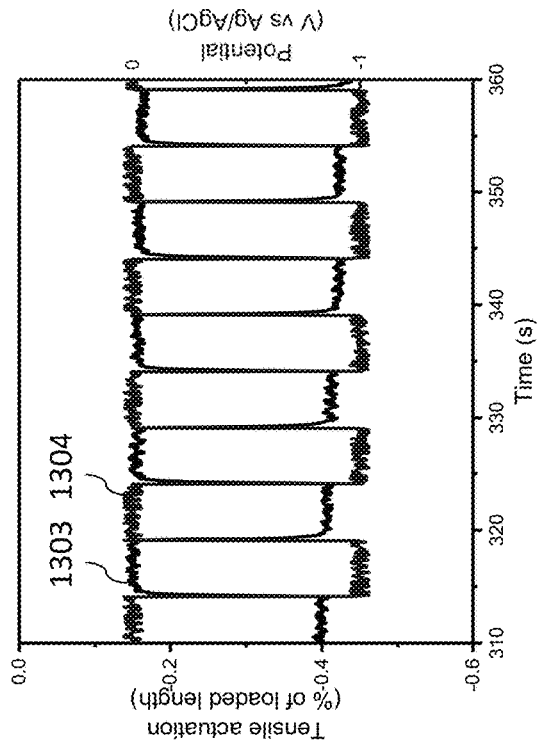

FIGS. 13A-C are graphs showing the time dependence of tensile stroke (lines 1301, 1303, and 1305, respectively), as a percent of loaded muscle length, for different changes in the 0.1 Hz applied potential (lines 1302, 1304, and 1306, respectively, versus a Ag/AgCl reference electrode) for isobaric electrochemical actuation of the n-doped coiled CNT yarn of FIG. 11 in an 0.1 M LiCl aqueous electrolyte. The applied stress was 12 MPa and the potential changes were +1 to −1 V for FIG. 13A, −1 to 0 V for FIG. 13B, and +1 to 0 V for FIG. 13C. Changing the potential (vs. Ag/AgCl) from +1 to −1 V provides a contractile stroke of 1.4% for the functionalized n-doped coiled CNT yarn. When potential changes from +1 to 0 V and from 0 to −1 V were applied, contractile strokes of 0.3% and 0.25% were obtained. The monotonic increase and decrease in contractile stroke with decrease and increase in applied potential, respectively, indicates unipolar-stroke behavior. This behavior contrast with that for the electrochemically actuation of the pristine coiled CNT yarn, which typically show a quasi-parabolic dependence of muscle stroke on applied potential. A elongation occurs in the region from +1 to 0 V, and a contraction occurs in the region from 0 to +1 V, which results in partial stroke cancellation when the potential is scanned from extreme positive values to extreme negative values. Strokes at both positive and negative potentials additively contribute to the total stroke for the functionalized n-doped coiled CNT yarn. As a result, the stroke for the n-doped functionalized coiled CNT yarn was about 2 times that for the pristine CNT coiled yarn when both yarns were actuated in the 0.1 M LiCl aqueous electrolyte.

Figure 14A:
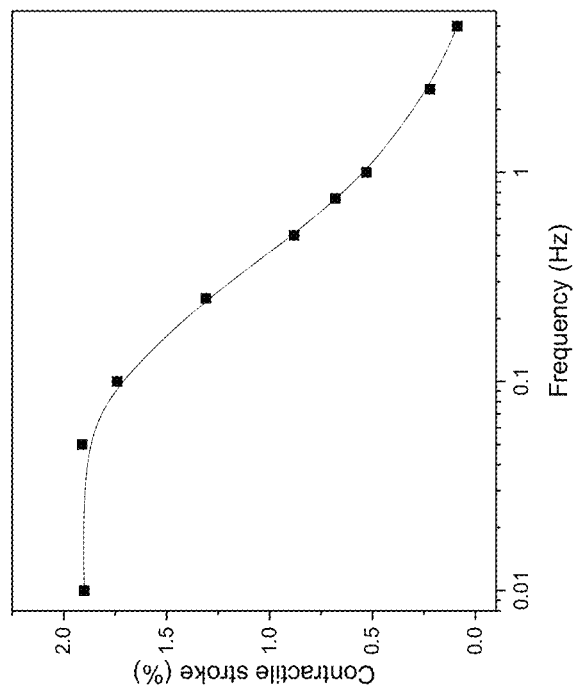
FIG. 14A is a graph showing the tensile actuation of the n-doped coiled CNT yarn of FIG. 11, when driven by cyclic voltammetry between +1 and −1 V (versus an Ag/AgCl reference electrode).
Figure 14B:
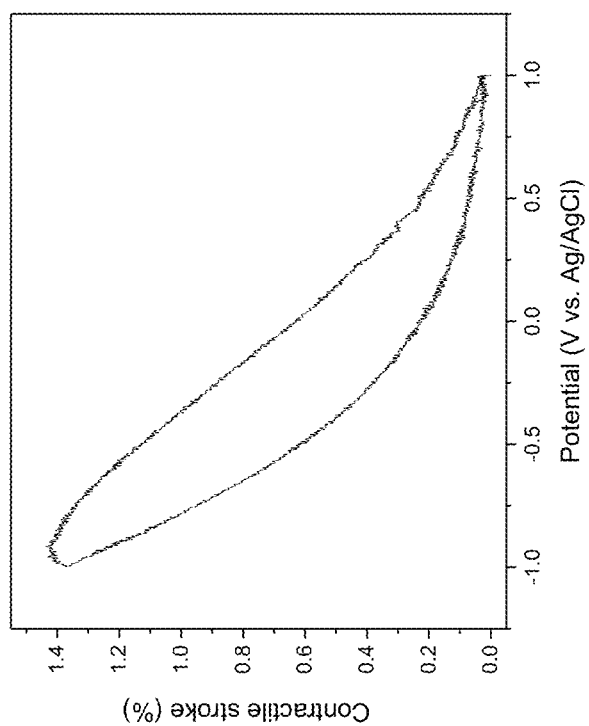
FIG. 14B is graph showing the dependence of actuator stroke on frequency for an applied square wave potential of +1 to −1 V (versus a Ag/AgCl reference electrode) for the n-doped coiled CNT yarn of FIG. 11.

The tensile stroke of the nitric acid oxidized yarn of FIG. 11 was characterized by cyclic voltammetry scans (vs. Ag/AgCl) at a scan rate of 25 mV/s (FIG. 14A). Note that the stroke behavior versus applied potential for the functionalized coiled CNT yarn is unipolar with respect to that for the pristine CNT coiled yarn at positive potentials, enabling additive stroke contribution from extreme positive potentials to extreme negative potentials. These results indicate that only positive ions are injected and removed at all potentials in the redox stability window for the functionalized coiled CNT yarn. Such behavior is a result of the shift of the pzc to above +1 V (vs. Ag/AgCl). The stroke of this functionalized CNT coiled yarn muscle decreases with increasing cycle frequency (FIG. 14B). More specifically, the stroke decreases from 1.8% to 0.1% as the cycle frequency increases from 0.01 Hz to 5 Hz. Unlike for PSS@CNT coiled yarn, which increases and then decreases stroke with increasing frequency, the stroke of the functionalized coiled CNT yarn decreases monotonically with increasing frequency.

Coiled, unipolar stroke artificial muscles can optionally be either homochiral or heterochiral, where homochiral means that the chirality of yarn twist is the same as the chirality of yarn coiling, and heterochiral means that the chirality of yarn twist is opposite to the chirality of yarn coiling. The benefit of using these different configurations is that a homochiral yarn contracts during electrochemically-produced volume increase, whereas a heterochiral yarn elongates during electrochemically-produced volume increase.

Coiling, as a result of inserting extreme twist into a yarn or by wrapping a twisted yarn around a mandrel, can be usefully employed to vary muscle stroke. Coiling by inserting extreme twist, which results in a homochiral muscle, is especially preferred. This coiling is characterized by a spring index, which is defined as the ratio of the average coil diameter to the diameter of the yarn that comprises the coil. Use of large spring index muscles increases muscle stroke, but decreases the force that the muscle can generate. For realizing large muscle stroke, coil indices above 1.5 are preferred. On the other hand, coil indices below 1.5 are preferred for increasing load-carrying capabilities during actuation.

For the same reason that unipolar stroke yarns are especially useful for tensile actuation, they are preferred for torsional actuation. This reason is that, in both cases, the potential range of the electrochemical window that can be used for a stroke in one direction is expanded. Various geometries for realizing torsional actuation of electrochemically-powered artificial muscles have been previously described, which can be used for the present invention embodiments. These torsionally-actuating, twisted, unipolar-stroke muscles can optionally be non-coiled, coiled, plied, or combinations thereof.

The application possibilities for the unipolar-stroke artificial muscles are diverse, and include powerful, large-stroke muscles for robotics, prosthetics, exoskeletons, and morphing textiles. While passive, moisture-responsive and temperature-responsive muscle yarns are especially useful for environmentally-powered textiles that change porosity according to comfort needs, the present electrochemically-powered, unipolar-stroke muscles can be actively used for both of these applications and for clothing that provides actuation in wearable assistive devices to improve the mobility of especially the elderly.

Because of their large strokes, which result from the unipolar-stroke behavior, these unipolar-stroke muscles are especially preferred among the general category of electrochemical muscles. Moreover, electrochemical muscles have major advantages over muscles that are electrothermally actuated in that: (1) they have a natural latching state in which electrical power is not required to maintain muscle stroke, (2) electrical energy is stored during charging to drive actuation and can be easily recovered when actuation is reversed, and (3) they are easily scalable by placing muscles, comprising both anode and cathode components, in parallel.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. The scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

Amounts and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about" and "substantially" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "substantially perpendicular" and "substantially parallel" is meant to encompass variations of in some embodiments within ±10° of the perpendicular and parallel directions, respectively, in some embodiments within ±5° of the perpendicular and parallel directions, respectively, in some embodiments within ±1 of the perpendicular and parallel directions, respectively, and in some embodiments within ±0.5° of the perpendicular and parallel directions, respectively.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

REFERENCES

J. N. Barisci et al., "Increased actuation rate of electromechanical carbon nanotube actuators using potential pulses with resistance compensation," *Smart Materials and Structures* 12, 549 (2003) ("Barisci 2003").

J. N. Barisci et al., "Electrochemical characterization of single-walled carbon nanotube electrodes," *Journal of the Electrochemical Society* 147, 4580-4583 (2000) ("Barisci 2000").

R. H. Baughman et al., "Carbon nanotube actuators," *Science* 284, 1340-1344 (1999) ("Baughman 1999").

R. H. Baughman, "Conducting polymer artificial muscles," *Synthetic Metals* 78, 339-353 (1996) ("Baughman 1996").

L. Bay et al., "A conducting polymer artificial muscle with 12% linear strain," *Advanced Materials* 15, 310-313 (2003) ("Bay 2003").

H. Finkelmann et al., in *Smart Structures and Materials 2002: Electroactive Polymer Actuators and Devices (EAPAD)* (International Society for Optics and Photonics, 2002), vol. 4695, pp. 459-465 ("Finkelmann 2002").

J. Foroughi et al., "Torsional carbon nanotube artificial muscles," *Science* 334, 494-497 (2011) ("Foroughi 2011").

C. S. Haines et al., "Artificial muscles from fishing line and sewing thread, *Science* 343, 868-872 (2014) ("Haines 2014").

I. Hunter et al., Technical Digest of Solid-State Sensor and Actuator Workshop, *South Carolina, USA: Hilton Head Island,* 178-185 (1992) ("Hunter A 1992").

I. W. Hunter et al., in *Solid-State Sensor and Actuator Workshop,* 1992. *5th Technical Digest, IEEE* (IEEE, 1992), pp. 178-185 ("Hunter B 1992").

K. J. Kim et al., "Enhancing the work capacity of electrochemical artificial muscles by coiling plies of twist-released carbon nanotube yarns," *ACS Applied Materials & Interfaces* 11, 13533-13537 (2019) ("Kim 2019").

S. H. Kim et al., "Harvesting electrical energy from carbon nanotube yarn twist," *Science* 357, 773-778 (2017) ("Kim 2017").

C. Kim et al., "Electrochemical properties of carbon nanofiber web as an electrode for supercapacitor prepared by electrospinning," *Applied Physics Letters* 83, 1216-1218 (2003) ("Kim 2003").

J. A. Lee et al., "Electrochemically powered, energy-conserving carbon nanotube artificial muscles," *Advanced Materials* 29, 1700870 (2017) ("Lee 2017").

M. D. Lima et al., "Electrically, chemically, and photonically powered torsional and tensile actuation of hybrid carbon nanotube yarn muscles," *Science* 338, 928-932 (2012) ("Lima 2012").

M. D. Lima et al., "Biscrolling nanotube sheets and functional guests into yarns," *Science* 331, 51-55 (2011) ("Lima 2011").

J. D. Madden et al., in *Smart Structures and Materials 2002: Electroactive Polymer Actuators and Devices (EAPAD)* (International Society for Optics and Photonics, 2002), vol. 4695, pp. 176-191 ("Madden 2002").

S. J. Murray et al., "6% magnetic-field-induced strain by twin-boundary motion in ferromagnetic Ni—Mn—Ga," *Applied Physics Letters* 77, 886-888 (2000) ("Murray 2000").

S. Nemat-Nasser et al., "Comparative experimental study of ionic polymer-metal composites with different backbone ionomers and in various cation forms," *Journal of Applied Physics* 93, 5255-5267 (2003) ("Nemat-Nasser 2003").

E. Nightingale Jr, "Phenomenological theory of ion solvation. Effective radii of hydrated ions," *The Journal of Physical Chemistry* 63, 1381-1387 (1959) ("Nightingale 1959").

J. Qiao et al., "Large-stroke electrochemical carbon nanotube/graphene yarn muscles, *Small* 14, 1801883 (2018) ("Qiao 2018").

D. K. Shenoy et al., "Carbon coated liquid crystal elastomer film for artificial muscle applications," *Sensors and Actuators A: Physical* 96, 184-188 (2002) ("Shenoy 2002").

A. Sozinov et al., "Giant magnetic-field-induced strain in NiMnGa seven-layered martensitic phase,"*Applied Physics Letters* 80, 1746-1748 (2002) ("Sozinov 2002").

D. L. Thomsen et al., "Liquid crystal elastomers with mechanical properties of a muscle," *Macromolecules* 34, 5868-5875 (2001) ("Thompsen 2001").

R. Tickle et al., "Magnetic and magnetomechanical properties of $Ni_2MnGa$," *Journal of Magnetism and Magnetic Materials* 195, 627-638 (1999) ("Tickle 1999").

M. Zhang et al., "Multifunctional carbon nanotube yarns by downsizing an ancient technology," *Science* 306, 1358-1361 (2004) ("Zhang 2004").

E. Zussman et al., "Mechanical and structural characterization of electrospun PAN-derived carbon nanofibers," *Carbon* 43, 2175-2185 (2005) ("Zussman 2005").

What is claimed is:

1. An electrochemical artificial muscle comprising:
   (a) an actuating electrode that comprises a first twisted yarn or coiled yarn that is electrically conducting;
   (b) an electronically conducting counter electrode;
   (c) an ionic conductor that provides a path for ionic conduction between said actuating electrode and said counter electrode;
   (d) a material that shifts the potential of zero charge of the actuating electrode, wherein (i) the shift in potential increases the potential range over which the actuating electrode monotonically increases or monotonically decreases actuator stroke during increase in potential, and
(ii) the first twisted or coiled yarn in the electrochemical artificial muscle has a monotonic potential range fraction of at least 0.7.

2. The electrochemical artificial muscle of claim 1, wherein the first twisted yarn or coiled yarn is (i) an electronically conducting twisted yarn or coiled yarn or (ii) a twisted yarn or coiled yarn having an electronically conducting sheath.

3. The electrochemical artificial muscle of claim 1, wherein the first twisted or coiled yarn has a capacitance of at least 0.1 F/g.

4. The electrochemical artificial muscle of claim 1, wherein the first twisted or coiled yarn is a twisted and coiled yarn in which a twisted yarn is coiled.

5. The electrochemical artificial muscle of claim 4, wherein the twisted and coiled yarn has a spring index below 1.5 or above 3.

6. The electrochemical artificial muscle of claim 1, wherein the material comprises at least 10% of the total mass of the first twisted yarn or coiled yarn.

7. The electrochemical artificial muscle of claim 1, wherein the material is at least partially covalently attached, directly or indirectly, to the first twisted yarn or coiled yarn.

8. The electrochemical artificial muscle of claim 1, wherein the material is an ion-exchange material.

9. The electrochemical artificial muscle of claim 1, wherein the material comprises a layer of organic or inorganic material that is not substantially directly or indirectly covalently attached to the actuating electrode.

10. The electrochemical artificial muscle of claim 1, wherein the electrochemical artificial muscle is coiled and is operable to provide a tensile stroke of at least 2% when electrochemically charged in an aqueous or non-aqueous electrolyte.

11. The electrochemical artificial muscle of claim 1, wherein the material comprises an ionic polymer.

12. The electrochemical artificial muscle of claim 1, wherein
(a) the electrochemical artificial muscle comprises two or more constituent actuating electrodes,
(b) one or more constituent actuating electrodes can operate as an anode,
(c) one or more constituent actuating electrodes can operate as a cathode, and
(d) the anode and cathode actuating electrodes are connected through an ionic conductor.

13. The electrochemical artificial muscle of claim 12, wherein the constituent actuating electrodes are mechanically coupled together.

14. The electrochemical artificial muscle of claim 1, wherein the electronically conducting counter electrode is a second yarn.

15. The electrochemical artificial muscle of claim 14, wherein
(a) the second yarn comprises a twisted, electrically conducting nanofiber yarn, and
(b) the material is a layer on the electrically conducting nanofibers of the nanofiber yarn.

16. The electrochemical artificial muscle of claim 1, wherein
(a) the electrochemical artificial muscle can be operated as a torsional muscle, and
(b) opposite muscle ends of the electrochemical artificial muscle are not tethered to prohibit relative rotation.

17. An electrochemical artificial muscle comprising:
(a) an actuating electrode that comprises a first twisted yarn or coiled yarn that is electrically conducting;
(b) an electronically conducting counter electrode;
(c) an ionic conductor that provides a path for ionic conduction between said actuating electrode and said counter electrode;
(d) a material that shifts the potential of zero charge of the actuating electrode, wherein
(i) the shift in potential increases the potential range over which the actuating electrode monotonically increases or monotonically decreases actuator stroke during increase in potential,
(ii) the electrochemical artificial muscle is surrounded by electrolyte comprising a solvating species, and
(iii) the electrochemical artificial muscle operates in the electrolyte.

18. The electrochemical artificial muscle of claim 17, wherein the electrochemical artificial muscle has an actuator stroke that increases over a potential scan rate range with increasing potential scan rate, as a result of the material and the electrolyte surrounding the electrochemical artificial muscle.

19. An electrochemical artificial muscle comprising:
(a) an actuating electrode that comprises a first twisted yarn or coiled yarn that is electrically conducting;
(b) an electronically conducting counter electrode;
(c) an ionic conductor that provides a path for ionic conduction between said actuating electrode and said counter electrode;
(d) a material that shifts the potential of zero charge of the actuating electrode, wherein
(i) the shift in potential increases the potential range over which the actuating electrode monotonically increases or monotonically decreases actuator stroke during increase in potential,
(ii) the electrochemical artificial muscle can be operated as a tensile muscle, and
(iii) opposite muscle ends of the electrochemical artificial muscle are tethered to prohibit relative rotation.

* * * * *